(12) United States Patent
Krom et al.

(10) Patent No.: US 9,138,284 B2
(45) Date of Patent: Sep. 22, 2015

(54) ELECTROSURGICAL TOOL COVER

(75) Inventors: Justin Krom, Southington, CT (US);
Kenneth L. Gong, San Jose, CA (US);
Richard D. Gresham, Guilford, CT
(US); Scott E. Manzo, Shelton, CT
(US); Joseph P. Orban, III, Norwalk,
CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1102 days.

(21) Appl. No.: 13/167,876

(22) Filed: Jun. 24, 2011

(65) Prior Publication Data
US 2012/0010611 A1    Jan. 12, 2012

Related U.S. Application Data

(60) Provisional application No. 61/362,916, filed on Jul. 9, 2010.

(51) Int. Cl.
*A61B 17/00* (2006.01)
*A61B 18/14* (2006.01)
*A61B 19/00* (2006.01)
*A61B 18/00* (2006.01)

(52) U.S. Cl.
CPC ............. *A61B 18/1445* (2013.01); *A61B 19/40* (2013.01); *A61B 19/2203* (2013.01); *A61B 2018/00083* (2013.01)

(58) Field of Classification Search
CPC .................. A61B 2018/00083; A61B 18/1445; A61B 18/14; A61B 19/40; A61B 19/2203; A61B 2017/2829; A61B 2017/00336
USPC ............................................................ 606/41
See application file for complete search history.

(56) References Cited

U.S. PATENT DOCUMENTS 5,261,918 A * 11/1993 Phillips et al. ................ 606/140
5,415,157 A *  5/1995 Welcome ....................... 600/121
(Continued)

FOREIGN PATENT DOCUMENTS

EP    1738705 A1    1/2007
EP    2042117 A1    4/2009
(Continued)

OTHER PUBLICATIONS

U.S. Appl. No. 12/832,580, filed Jul. 8, 2010.
(Continued)

*Primary Examiner* — Michael Peffley

(57) ABSTRACT

A cover for an electrosurgical instrument having a wrist structure and an end effector is provided. The cover includes a hollow elongated structure, which includes a tip cover portion and a base cover portion integrally connected to the tip cover portion. The tip cover portion has a distal end with an opening therethrough sized to receive the end effector of the electrosurgical instrument and is composed of a first, electrically insulative material having a flexibility sufficient to allow the end effector to be manipulated while the end effector is received in the opening. The base cover portion is composed of a second material having a higher tear strength than the first material. The tip cover portion and the base cover portion overlap at an overlap region configured to receive the wrist structure of the electrosurgical instrument when the end effector is received in the opening.

30 Claims, 18 Drawing Sheets

(56) References Cited

U.S. PATENT DOCUMENTS

| | | | |
|---|---|---|---|
| 5,417,203 A | 5/1995 | Tovey et al. | |
| 5,491,882 A | 2/1996 | Walston et al. | |
| 5,624,392 A * | 4/1997 | Saab | 604/43 |
| 5,724,994 A * | 3/1998 | Simon et al. | 128/885 |
| 6,004,509 A | 12/1999 | Dey et al. | |
| 6,016,848 A | 1/2000 | Egres, Jr. | |
| 6,091,993 A * | 7/2000 | Bouchier et al. | 607/98 |
| 6,106,540 A * | 8/2000 | White et al. | 606/191 |
| 6,817,974 B2 | 11/2004 | Cooper et al. | |
| 6,994,708 B2 | 2/2006 | Manzo | |
| 7,320,700 B2 | 1/2008 | Cooper et al. | |
| 7,367,973 B2 * | 5/2008 | Manzo et al. | 606/41 |
| 7,785,252 B2 | 8/2010 | Danitz et al. | |
| 7,879,035 B2 * | 2/2011 | Garrison et al. | 606/51 |
| 2002/0072712 A1 | 6/2002 | Nool et al. | |
| 2003/0125719 A1 * | 7/2003 | Furnish | 606/15 |
| 2003/0163128 A1 | 8/2003 | Patil et al. | |
| 2004/0098040 A1 | 5/2004 | Taniguchi et al. | |
| 2004/0122462 A1 * | 6/2004 | Bakos et al. | 606/191 |
| 2004/0230204 A1 | 11/2004 | Wortley et al. | |
| 2005/0216033 A1 | 9/2005 | Lee et al. | |
| 2006/0025654 A1 * | 2/2006 | Suzuki et al. | 600/114 |
| 2006/0079884 A1 | 4/2006 | Manzo et al. | |
| 2006/0079934 A1 * | 4/2006 | Ogawa et al. | 606/205 |
| 2006/0247743 A1 * | 11/2006 | Hayakawa et al. | 607/89 |
| 2007/0005001 A1 | 1/2007 | Rowe et al. | |
| 2007/0112337 A1 * | 5/2007 | Salman et al. | 606/1 |
| 2007/0179486 A1 | 8/2007 | Welch et al. | |
| 2007/0239203 A1 * | 10/2007 | Cooper et al. | 606/205 |
| 2008/0046122 A1 | 2/2008 | Manzo et al. | |
| 2008/0306335 A1 | 12/2008 | Lau et al. | |
| 2009/0082628 A1 | 3/2009 | Kucklick et al. | |
| 2009/0088738 A1 * | 4/2009 | Guerra et al. | 606/41 |
| 2009/0088741 A1 * | 4/2009 | Hushka et al. | 606/41 |
| 2009/0088747 A1 | 4/2009 | Hushka et al. | |
| 2009/0177141 A1 | 7/2009 | Kucklick | |
| 2009/0182201 A1 | 7/2009 | Kucklick et al. | |
| 2009/0254162 A1 | 10/2009 | Quinci et al. | |
| 2009/0287194 A1 * | 11/2009 | Gertz et al. | 606/8 |
| 2010/0016852 A1 | 1/2010 | Manzo et al. | |
| 2010/0168510 A1 | 7/2010 | Rogers et al. | |
| 2010/0268163 A1 | 10/2010 | Rowe et al. | |
| 2012/0065472 A1 | 3/2012 | Doyle et al. | |
| 2012/0065645 A1 | 3/2012 | Doyle et al. | |
| 2013/0123805 A1 | 5/2013 | Park et al. | |
| 2014/0171943 A1 * | 6/2014 | Weitzner et al. | 606/41 |

FOREIGN PATENT DOCUMENTS

| | | |
|---|---|---|
| JP | 2010075565 A | 4/2010 |
| WO | WO-2005032642 A2 | 4/2005 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

PCT/US2011/041842 International Search Report and Written Opinion of the International Searching Authority, mailed Oct. 31, 2011, 10 pages.

* cited by examiner

ELECTROSURGICAL TOOL COVER

CROSS-REFERENCE TO RELATED APPLICATIONS

This application claims the benefit of U.S. Provisional Application No. 61/362,916, filed Jul. 9, 2010, which is hereby incorporated by reference herein in its entirety.

TECHNICAL FIELD

The present teachings are generally directed to electrosurgical instruments or tools. More particularly, aspects of the present teachings relate to wristed electrosurgical instrument tool covers that can inhibit or prevent conduction of electrical current from an electrically live wristed tool to the patient or other undesirable locations near the surgical site.

INTRODUCTION

Various electrosurgical treatment instruments, which generally use high-frequency alternating current, treat tissue of an organism, e.g., a human patient, using heat produced by electrical energy while cutting, shearing, grasping, or contacting the tissue. Such instruments are used to perform a variety of treatments, such as, for example, incision, coagulation, ablation, and the like in minimally invasive procedures, either performed manually or via robotic surgical systems. Electrosurgical treatment and cutting instruments for open surgery, manually performed endoscopic surgery and robotically controlled instruments have been described. However, electrosurgical treatments performed via minimally invasive (e.g., endoscopic) surgery can be riskier than traditional open procedures.

For example, monopolar electrosurgery creates a complete electrical circuit from the active electrode, to the target tissue, to the return electrode, and back to the generator. An exemplary monopolar surgical instrument is described in U.S. Pat. No. 6,994,708 filed Apr. 18, 2002, the entire disclosure of which is incorporated herein by reference. In some cases, surgeons work through incisions and manipulate such electrosurgical instruments through a cannula. Such an approach, however, can pose difficulties in attempting to prevent the electricity generated by the instrument from traveling outside the desired path and burning tissue at an undesired location, e.g., away from the end effector.

Robotic surgical systems, for example the DA VINCI® system commercialized by Intuitive Surgical, Inc., also can utilize electrosurgical instruments (e.g., including monopolar cautery end effectors) to perform minimally invasive electrosurgical procedures robotically. The electrosurgical instruments in these systems also can be used to dessicate tissue by applying current to a heat conductive end effector, where the heat conductive end effector is used, for example, in procedures to stop bleeding from small vessels via sealing or coagulation, or to cut through soft tissue via ablation to perform minimally invasive surgery. For example, as described in U.S. Patent Application Publication No. US 2006/0079884 A1 (filed Apr. 13, 2006; entitled "Robotic Tool with Wristed Monopolar Electrosurgical End Effectors"), incorporated in its entirety herein by reference, an electrosurgical instrument includes an elongate shaft having a proximal end and a distal end. Further, an electrically live wrist member or combination of wrist components is disposed at the distal end portion of the shaft, and an electrocautery end effector is mounted to the wrist member. An interface is disposed at the proximal end of the shaft. An electrical conductor extends from the interface to the end effector so as to deliver electrical energy and associated heat to tissue engaged by the end effector.

The electrocautery end effector can include a variety of elements formed from electrically conductive materials, such as, for example, metal (e.g., stainless steel, and the like). For example, the end effector can include a pair of cooperative tissue shearing blades, with one of the blades communicating electrically with a conductor so as to deliver electrical energy to tissue engaged by the end effector (monopolar cautery). In various other exemplary embodiments, the end effector can include a scalpel, blade, hook, spatula, probe, needle point, dissectors, graspers, movable jaws (e.g., clamp), and any other type of surgical end effector equipment configured to manipulate and/or cauterize tissue and the like.

The mechanical wrist structure, which is made of a variety of suitable materials that can be electrically conductive, including metal (e.g., stainless steel and like) materials, is operational in a wet environment, and as mentioned above, is coupled to the electrocautery end effector in order to enhance maneuverability and positioning of the end effector.

Due to the use of electrical elements and conduction of electricity through various portions of the electrosurgical instrument, insulation material is disposed over the wrist member so as to inhibit conduction of electrical current from the electrically live wrist member to the patient, thus preventing unwanted electrically-related patient burns at a location away from the electrocautery end effector, particularly the area around the wrist member.

In some electrosurgical applications, an insulation material for electrocautery devices is provided as a cover that is placed over the electrically live wrist and a portion of the end effector, and the cover has an outer diameter substantially the same as that of the shaft of the electrosurgical instrument. The cover is intended to be permanent or removable and potentially reusable (e.g., after sterilization). The wrist member can have a compact or smaller outer diameter than the instrument outer diameter, which can allow for a cover having a relatively large wall thickness while still maintaining an overall outer diameter at the distal end of the instrument, for example, that enables the instrument to be delivered through a cannula or other narrow passage.

Aside from providing an electrosurgical tool cover configuration that avoids undesired electrical conduction, numerous other design considerations arise in the context of minimally invasive and/or robotically controlled electrosurgical applications. Some examples of the challenging design considerations that are presented in minimally invasive and/or robotically controlled electrosurgery applications include the narrow passages (e.g., cannulas, body orifices, body tissue geometry) in which instruments are advanced and operated, the relatively wide and varied range of angular movement of the wrist that is desired, the wet environment (e.g., blood, saline, etc.) in which the instruments must operate, the high electrical energy and temperature ranges in which the instruments operate, the repeated (e.g., cyclical) movement to which the wrist and end effector are subjected, and/or the abrasive and/or relatively high impact forces that can be exerted on the instrument during operation, for example, as a result of collision with other instruments, bone, and/or sharp edges of various objects (such as the end of the cannula when the instrument is withdrawn). Complicating things even further is the fact that many of these design considerations compete with one another such that finding an optimal solution to address one issue may negatively impact a solution to another.

While current insulative electrosurgical instrument tool covers can prevent much of the conduction of electrical current from the electrically live wrist member to the patient, still further improvements are desirable to address the challenges discussed above, as well as others. In general, it is desirable to provide an electrosurgical tool cover that improves the cover's performance with regard to maintaining a secure and proper fit over the instrument tool, impact, scratch resistance, tear resistance, and durability, while substantially maintaining a sufficient range of motion of wrist articulation (e.g., providing sufficient flexibility), dielectric strength or insulation properties, and high temperature capability which are preferably utilized in the course of robotic and/or minimally invasive surgery.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments of the present teachings, the present teachings contemplate a cover for an electrosurgical instrument having a wrist structure and an end effector. The cover includes a hollow elongated structure. The hollow elongated structure includes a tip cover portion and a base cover portion. The tip cover portion has a distal end with an opening therethrough sized to receive the end effector of the electrosurgical instrument and is composed of a first, electrically insulative material having a flexibility sufficient to allow the end effector to be manipulated while the end effector is received in the opening. The base cover portion is integrally connected to the tip cover portion and is composed of a second material having a higher tear strength than the first material. The tip cover portion and the base cover portion overlap at an overlap region configured to receive the wrist structure of the electrosurgical instrument when the end effector is received in the opening.

In accordance with at least one exemplary embodiment, the present teachings contemplate a cover for an electrosurgical instrument having a wrist structure and an end effector. The cover includes a hollow elongated composite material structure having an end with an opening therethrough sized to receive the end effector of the electrosurgical instrument. The hollow structure includes a first distal region, a second proximal region and a transition region in which the first material surrounds the second material. The first distal region includes the end with the opening and is composed of a first electrically insulative material having a flexibility sufficient to allow the end effector of the electrosurgical instrument to be manipulated while the end effector is received in the opening. The second proximal region is composed of a second material having a higher tear strength than the first material. The transition region is disposed between the first distal region and the second proximal region.

In accordance with at least one exemplary embodiment, the present teachings contemplate a cover for an electrosurgical instrument having a wrist structure and an end effector. The cover includes a hollow elongated composite material structure having an end with an opening therethrough sized to receive the end effector of the electrosurgical instrument. The hollow structure includes a first distal region, a second proximal region and a transition region in which the first material surrounds the second material. The first distal region includes the end with the opening and is composed of a first electrically insulative material having a flexibility sufficient to allow the end effector of the electrosurgical instrument to be manipulated while the end effector is received in the opening. The second proximal region is composed of a second material having a higher tensile strength than the first material. The transition region is disposed between the first distal region and the second proximal region.

Additional aspects and advantages will be set forth in part in the description which follows, and in part will be obvious from the description, or may be learned by practice of the present teachings. The objects and advantages may be realized and attained by means of the elements and combinations particularly pointed out in the appended claims and their equivalents.

It is to be understood that both the foregoing general description and the following detailed description are exemplary and explanatory only and are not restrictive of the claims.

BRIEF DESCRIPTION OF THE DRAWINGS

The present teachings can be understood from the following detailed description either alone or together with the accompanying drawings. The drawings are included to provide a further understanding of the present teachings, and are incorporated in and constitute a part of this specification. The drawings illustrate one or more embodiments of the present teachings and, together with the description, serve to explain certain principles and operation. In the drawings.

DETAILED DESCRIPTION

This description and the accompanying drawings illustrate exemplary embodiments and should not be taken as limiting, with the claims defining the scope of the present teachings. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the electrosurgical instrument.

For the purposes of this specification and appended claims, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Figure 1A:
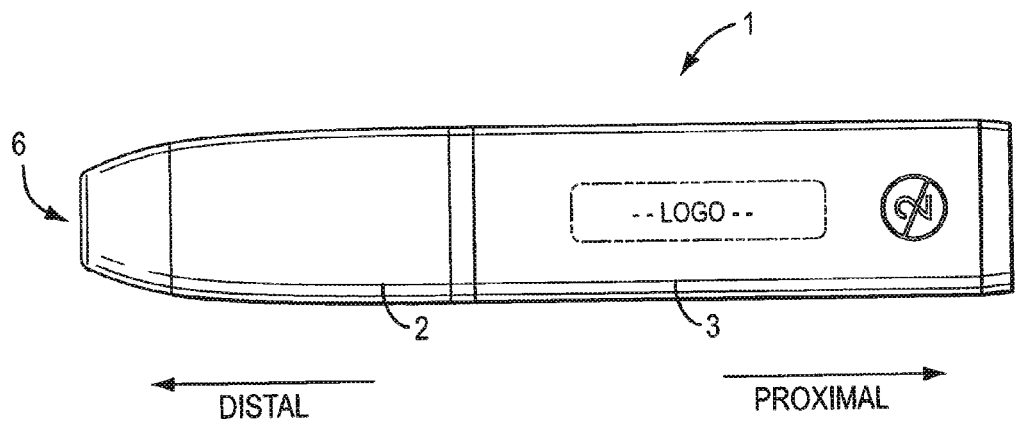
FIGS. 1A and 1B show side and perspective views, respectively, of an electrosurgical tool cover in accordance with an exemplary embodiment of the present teachings.
Figure 3A:
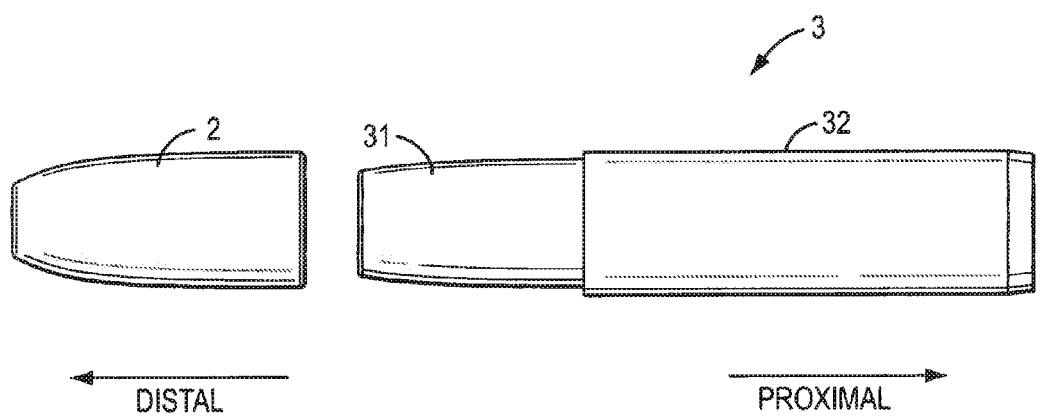
FIGS. 3A and 3B show exploded side and perspective views, respectively, of the exemplary electrosurgical tool cover's principal composite parts in accordance with an exemplary embodiment of the present teachings.
Figure 12:
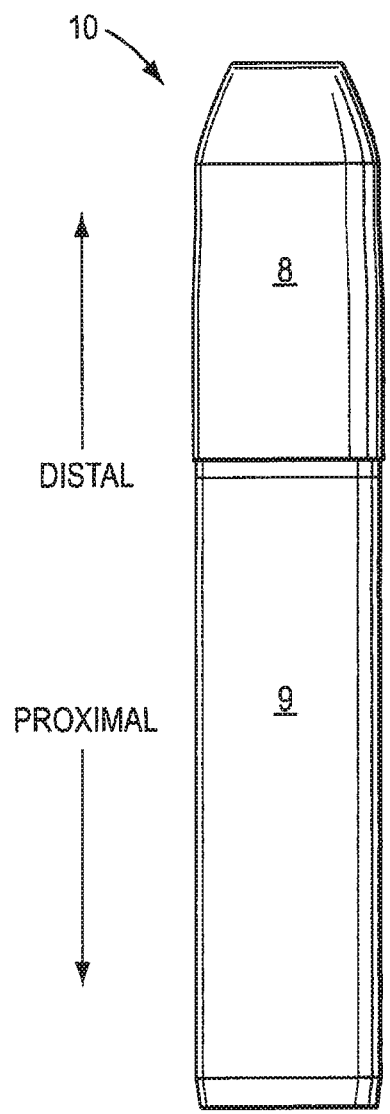
FIG. 12 is a side view of another exemplary embodiment of an electrosurgical tool cover in accordance with the present teachings.

The terms "proximal" and "distal" are relative terms, where the term "distal" refers to the portion of the object furthest from an operator of the instrument and closest to the surgical site, such as the opening of the tool cover or the end effector of the instrument. The term "proximal" indicates the relative proximity to the operator of the surgical instrument and refers to the portion of the object closest to the operator and furthest from the surgical site. To further illustrate these terms, the "proximal" and "distal" directions of the tool cover in accordance with various exemplary embodiments of the present teachings are illustrated in FIGS. 1A, 3A, and 12.

As mentioned above, the desired operation of wristed electrosurgical instruments, and the associated environments in which they operate, when performing robotically-controlled and/or minimally invasive procedures poses a variety of challenges to current tool covers for such instruments. To effectively protect the electrosurgical instrument and the patient during an electrosurgical procedure, electrosurgical instrument tool covers in accordance with the present teachings are configured to meet numerous competing and challenging design considerations, including those described above and further below, for example, to provide an effective and robust tool cover that addresses the numerous issues present in electrosurgical applications.

In many electrosurgical applications, such as, for example, when using electrocautery instruments, cautery energy levels are typically very high, and problems can arise when a tool cover does not provide sufficient electrical insulation, thereby posing a risk of burning and/or conducting electricity to the patient or conducting electricity to undesired locations (e.g., via direct contact or arcing). For example, in monopolar cautery applications, voltages can range from at least about 1000 volts to about 9000 volts. Also, the associated high temperatures in these applications can exceed 1000° F. at the arc coming out of an electrocautery end effector, with temperatures of liquid (e.g., blood, saline, etc.) in the surrounding environment reaching boiling levels (e.g., from about 212° F. to about 220° F.). The high temperatures associated with these applications can melt, deform, or burn various materials exposed to the same. In addition, while some materials can provide adequate insulative properties and sufficiently withstand high temperatures, some of those same materials are still susceptible to "arc tracking", which is a phenomenon where an electric current burns the top layer of an insulation material and allows the current to migrate across the insulation (e.g., along the length of a portion of the instrument shaft). Thus, while a material may be a good insulator, the material may allow or promote arc tracking, which is problematic in the surgical environment.

Additionally, the wet environments (e.g., including environments comprising blood, saline, etc.) of electrosurgical applications pose various challenges. For example, various materials when placed in such an environment are sufficiently hydrophilic such that the material "wets out," causing liquid to collect along a surface of the material. Such collection of liquid can form an electrically conductive pathway for the electrical energy from the instrument, for example, along an outer surface of a tool cover. As such, this "wetting out" can promote arc tracking through the fluid pathways. Also, wet environments may degrade the performance of a tool cover, depending on the material used. For instance, when moisture is absorbed into materials in high temperature environments, many materials break down due to the combination of the high temperature and the absorbed liquid. In addition, a tool cover could relax on the instrument and become loose, or start arc tracking, as a result of moisture absorption.

Yet another challenging design constraint in the context of robotically controlled and/or minimally invasive surgical applications includes the manipulation of electrosurgical instruments, which can involve a variety of ranges of motion (ROM), cycles of such ROMs, and/or a relatively large degree of ROMs. Thus, as an electrosurgical instrument is manipulated within an insulative tool cover, particularly at wrist members, current tool covers may be susceptible to break down, crack, tear, deform, and/or otherwise become damaged. In particular, when the wrist or wrist components of the electrosurgical instrument is pitched or yawed to operate the instrument, the wrist movement puts stress on the tool cover and also may cause the cover to pinch within portions of the wrist or strain at portions of the wrist that move against the cover when the instrument is in use. Additionally, when the wrist is moved, if the cover does not fold in the proper orientation, the wrist may pinch the cover, resulting in tears or limitations in the range of motion. However, if the cover does not have an adequate level of flexibility, then the range of motion of the wrist will be limited.

Also, because it may be desirable for the tool cover to extend over a portion of the end effector of the electrosurgical instrument, if the cover is not sufficiently flexible, then the cover may not maintain proper coverage over the end effector when the end effector is in a fully pitched or fully yawed position. In addition, after being manipulated into a fully pitched or fully yawed position, when the end effector is closed, for example, some portions of the cover may not reform and instead may become permanently stretched or otherwise deformed. Such stretching or permanent deformation increases the risk of tearing and/or otherwise damaging the tool cover, which ultimately can lead to ineffective electrical insulation.

Challenges also arise as a result of the narrow passages and spaces typically associated with robotically-controlled and/or minimally invasive electrosurgical applications. For example, when used in conjunction with a cannula for insertion and removal, in some cases the wrist holding the end effector of the electrosurgical instrument may not be straightened prior to retracting the instrument back through the cannula. In such circumstances, the tool cover may collide with portions of the cannula, and the impact can cause the cover to tear or rip. Also, due to the typically small and fixed sizes of cannulas, overall outer dimensions of the electrosurgical instruments inserted therethrough must be less than the inner dimensions of the cannula (e.g., allowing for about a 0.05 to 0.50 mm clearance), consequently posing constraints on the permissible thickness of an insulative tool cover. Inside dimensions (diameter) of various cannulas that are used in minimally invasive electrosurgical applications range from about 2 mm to about 13 mm. Such constraints can negatively impact the overall durability (e.g., tear resistance) and/or insulative properties of the cover. Further, using multiple layers to form a tool cover can be challenging in light of the potential for delamination during use or after aging. For example, if layers were to begin to delaminate, jamming of the cover on the cannula could occur. If the layers separate, one of the layers could dislodge into the patient. Further, even when only one material is used, a cover may not adequately maintain retention forces, and the cover may fall off the electrosurgical instrument during surgery and be dislodged into the patient.

Aside from potential impact with a cannula, during surgery, the electrosurgical instrument can come into contact and impact with other instruments that are being used simultaneously during a procedure or may collide with bones, organs, etc. of the patient. Such undesired contact and/or impact poses a risk of piercing, tearing, or the like of a tool cover. Abrasion may occur both against the cover on the outside by bones, other instruments, etc. and also against the cover on the inside by the movement of the electrosurgical instrument, particularly at the wrist region, against the cover.

Another problem that can arise is the relaxation (creep) of a tool cover due to cyclical and/or relatively large degree of freedom motions to which tool covers are subjected during an electrosurgical procedure. Such relaxation poses a risk of the tool cover coming off or improperly fitting on the electrosurgical instrument, thereby increasing the overall risk to the patient.

Aspects of at least one embodiment are generally related to surgical instruments or tools, and more particularly to an electrosurgical tool cover and methods of installing the cover to an electrosurgical instrument. The electrosurgical tool covers in accordance with various exemplary embodiments of the present teachings incorporate various unique design features and combinations that enable them to satisfy the numerous, often competing, design constraints that are encountered in robotically-controlled and/or minimally invasive electrosurgical applications. For example, electrosurgical instrument tool covers in accordance with various exemplary embodiments can promote patient safety while maintaining the current range of motion of instrument wrist articulation. Electrosurgical tool covers in accordance with various exemplary embodiments of the present teachings provide a robust design that is well-suited to safely and effectively performing minimally invasive electrosurgical procedures.

In at least one exemplary embodiment, an electrosurgical tool cover for use with an electrosurgical instrument, more particularly to cover the electrically live wrist member and a portion of an electrocautery end effector, is provided. The cover inhibits conduction of current towards the patient's tissue at undesired locations.

The electrosurgical tool cover in various exemplary embodiments has a high dielectric strength, high elongation, high arc track resistance, and high temperature resistance.

In various exemplary embodiments, an electrosurgical tool cover comprises multiple layers of materials having differing properties. One of the layers reinforces the electrosurgical tool, providing a higher degree of impact and tear resistance around the wrist member of the surgical instrument, while another layer provides higher electrically insulative properties, flexibility, and temperature resistance. The layers can be molded together to form the cover, which may be configured to cover a wrist member of an electrosurgical instrument while permitting the wrist member to maintain a relatively large and varied range of motion that is desired for various minimally invasive and/or robotically controlled surgical procedures.

According to yet other exemplary embodiments, electrosurgical tool covers having multiple material layers can provide high durability and arc track resistant properties in comparison to some current tool covers, without a large increase in the electrosurgical cover tool wall thickness, more particularly the thickness of the wall at locations surrounding the wrist member of the surgical instrument. An increase in the wall thickness of the electrosurgical tool cover can lead to an increased difficulty in accessing the surgical site through a cannula or other narrow passage. Various exemplary embodiments maintain a relatively small overall outer diameter of the instrument (i.e., with the tool cover assembled to the instrument), while comprising several layers of different material which can meet other desired design characteristics. For example, durability can be increased with the outer diameter remaining small enough to traverse within a cannula or other narrow passages.

In various exemplary embodiments, electrosurgical tool covers are contemplated that provide a high degree of impact and tear resistance surrounding the wrist member of the electrosurgical instrument and a high temperature resistance surrounding the end effector of the electrosurgical instrument. For example, various electrosurgical tool covers in accordance with exemplary embodiments can include a tip cover portion and a base cover portion, wherein the tip cover portion is made of a material with higher temperature resistance than a base cover portion. The base cover portion can be made of a different material from, and have higher rigidity properties than, the tip cover portion. The tip cover portion and the base cover portion are arranged to mutually provide a tougher structure around the wrist and a more temperature resistant structure around the end effector of the surgical instrument.

In various exemplary embodiments, the electrosurgical tool cover structure is flexible enough to maintain an adequate range of motion of the wrist and the end effector and durable enough to sustain impact strength with the cannula, bones, and/or other instruments. For example, in various exemplary embodiments, the jaws of an end effector can open up to approximately 40 degrees. Also in various exemplary embodiments, the wrist can move in both the pitch and yaw directions to ±65 degrees about the respective neutral axis.

Electrosurgical tool covers in accordance with various exemplary embodiments also may be operational in wet, liquid-filled environments, wherein the cover can include a surface (e.g., a hydrophobic surface) that prevents liquid pathways from forming thereon, for example, via saline or blood. This hydrophobic quality can also prevent arc tracking resulting from the formation of such conductive pathways. The use of a hydrophobic material can also help to inhibit moisture absorption and consequent degradation due to such absorption during use (e.g., relaxing on the instrument and becoming loose, arc tracking, and/or otherwise deteriorating). Further, by providing a cover that maintains its integrity and retention on the electrosurgical instrument, the cover can maintain a seal to the electrosurgical instrument in order to prevent liquid from entering into undesired compartments along the electrosurgical instrument, which can cause undesired electric conductions and other damage or contamination to the instrument.

In accordance with various exemplary embodiments, an installation tool for assembling an electrosurgical tool cover to an electrosurgical instrument is provided. The installation tool can hold the electrosurgical cover tool to avoid contamination and/or impact during the assembly process. The installation tool simultaneously assists with the installation process of the electrosurgical cover tool with the electrosurgical instrument, for example, by enabling a better grip on the tool cover.

In yet various other exemplary embodiments, the present teachings contemplate connecting an electrosurgical instrument mounted on a robotic manipulator to a generator unit through which electrical energy (high voltage current) is delivered to an end effector that engages tissue and a wrist member. The wrist member can operate in a wet environment. As described above, conduction of electrical current can be inhibited from the wrist member or shaft of the electrosurgical instrument to the patient or to the back portion of the surgical instrument by a variety of electrical isolation components.

Electrosurgical instruments can further include a wrist member located proximate the distal end of the shaft of the instrument. The wrist member can support and control an end effector movement to at least one degree of freedom relative to the shaft. In some exemplary embodiments, the electrosurgical tool cover comprises features that provide locking and sealing mechanisms that assist in retaining the cover in an assembled position relative to an electrosurgical instrument while avoiding the unwanted movement of the cover and/or unwanted fluid/liquid access to parts of the instrument.

Turning now to the drawings, FIG. 1A through FIG. 3A illustrate an exemplary embodiment of an electrosurgical tool cover 1. The cover 1 is configured to be placed over an electrosurgical instrument's distal end (see, e.g., FIGS. 10 and 11), which is the part closest to the surgical site, in order to cover and electrically insulate the electrosurgical instrument's electrical element, such as, for example, an electrically live wrist member and at least a portion of an electrocautery end effector. The electrosurgical tool cover 1 is reinforced by providing a composite structure that includes multiple layers of materials that provide insulation properties which can withstand high temperatures, inhibit arc-tracking, and have high dielectric strength. A more complete and detailed explanation of the structure and assembly is provided below.

Figure 1B:
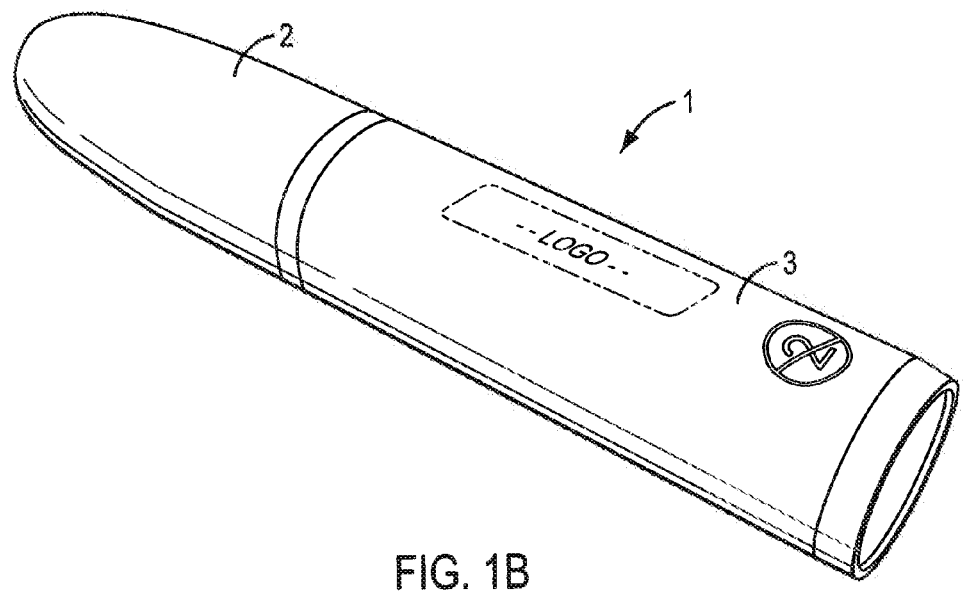

The electrosurgical tool cover 1 includes a reinforced multi-layer insulation cover comprising a tip cover portion 2 and a base cover portion 3 that are integrated together to form a single composite structure. FIG. 1A and FIG. 1B show side and perspective views of a hollow base cover portion 3 that is integrally attached (e.g., via overmolding) to a hollow tip cover portion 2 that has a generally tapered outer surface profile (e.g., a tapered curved surface of revolution); the defining proximal and distal boundaries need not be parallel nor planar nor continuous. As shown in FIG. 3A, the outer surface of the tip cover portion 2 also may be slightly curved such that it is slightly convex, particularly toward the distal end portion. The tip cover portion 2 has an outside diameter that decreases (tapers) toward the distal end of the tool cover 1. For example, in an exemplary embodiment, the outer diameter at the distal most end of the tip cover portion may range from about 0.150 inches to about 0.350 inches, for example, 0.200 inches.

The tip cover portion 2 has a distal end with an opening 6 (see, e.g., FIGS. 2A and 6) therethrough sized to receive the end effector of the electrosurgical instrument (not shown in FIGS. 1A-3A). The diameter of the opening 6 in an exemplary embodiment may be selected to prevent or inhibit pre-stressing the tip cover portion 2 of the tool cover 1 as it is placed over the distal end of the electrosurgical instrument, while also permitting an adequate range of movement of the end effector (e.g., a degree of freedom associated with jaw member movement, such as each of the shear blades) within the opening 6. In exemplary embodiments, the diameter of the opening 6 may range from about 1.5 mm to about 5.0 mm, for example, about 3.0 mm. The tip cover portion 2 is composed of a first, electrically insulative material having a flexibility sufficient to allow the end effector to be manipulated while the end effector is received in the opening 6. The end effector within the tip cover portion 2 is able to be manipulated and moved in a variety of directions, for example, depending on the movement of the wrist of the electrosurgical instrument or the opening/closing of the end effector. The tip cover portion 2 is configured to partially cover the end effector of the electrosurgical instrument when installed thereon (see FIG. 11, for example).

In an exemplary embodiment, the electrically insulative material of which the tip cover portion 2 is composed may be, for example, silicone, e.g., Dow Silicone Q7-4780. The selected material, such as silicone, meets many of the design constraints involved in providing an electrosurgical tool cover for an electrosurgical instrument. For example, the material, such as silicone, from which the tip cover portion 2 is made can retain its flexibility and resilience, resist high temperatures, and exhibit superior electrical properties that minimize and/or avoid arc tracking and provide relatively high electrical insulation, such as, for example, 425 Volts/mil.

In particular, the tip cover portion 2 acts as an insulator of the electrically charged end effector of the electrosurgical instrument, and a material such as silicone can provide a high dielectric strength in addition to being able to insulate against the high temperatures associated with use of the electrosurgical instrument to perform cautery (e.g., including monopolar cautery) procedures, for example. Silicone may be beneficially used as the first material because silicone can withstand very high temperatures, such as those used in cautery operations and mentioned above, and silicone overcomes the problems that occur with other types of materials in high temperature environments. Specifically, silicone is resistant to melting, deforming, and/or otherwise breaking down in wet environments, such as in blood, saline, or other liquid-filled environments, and allows for high continuous temperature use without material distortion.

Moreover, silicone is hydrophobic and has a surface tension that causes liquids to bead up on the surface, thus avoiding absorption of liquids and the formation of undesirable, conductive pathways on an outer surface thereof. This hydrophobic nature of silicone can prevent the tool cover 1, including its outer surface, from becoming electrically conductive. In addition, silicone provides for high arc track resistance, so that the tip cover portion 2 does not act as a conductor during use. Arc tracking may be caused by the formation of conductive liquid pathways on the surface of the tool cover 1 or by material breakdown of the material itself causing electrical conduction and arc tracking through the tool cover.

Figure 11:
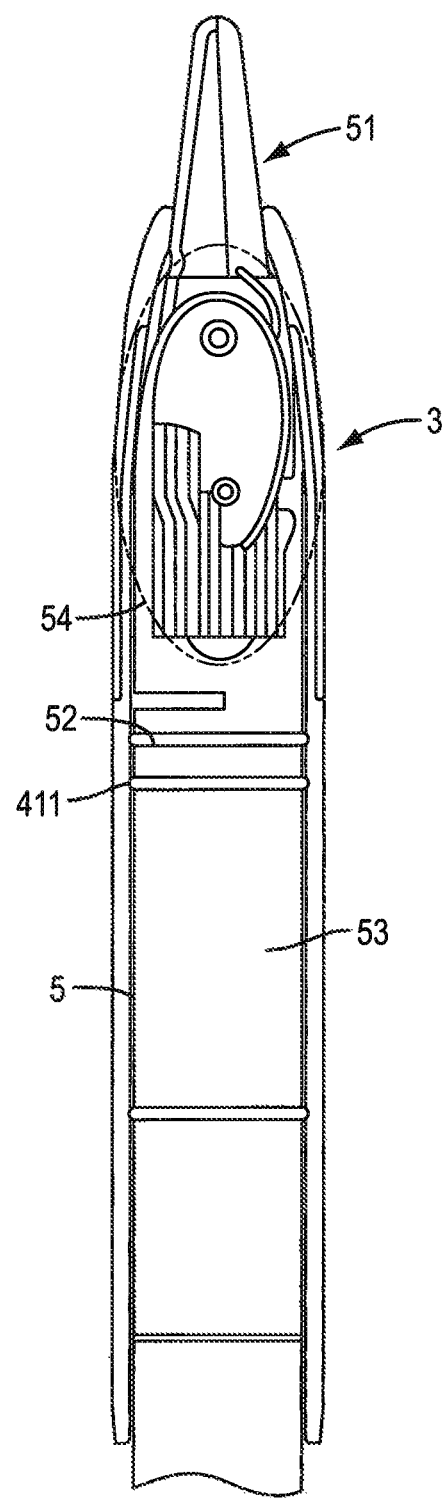
FIG. 11 is a cross-sectional view of the electrosurgical tool cover installed on the electrosurgical instrument of FIG. 10.

In addition to the properties described above, the material, such as silicone, from which the tip cover portion 2 is made, can be sufficiently flexible to permit the range of motion and maneuverability desirable for electrosurgical applications. As shown in FIG. 11, for example, the tip cover portion 2 of the tool cover 1 is configured to receive the end effector 51 of an electrosurgical instrument. The electrosurgical instrument 5 may also include a wrist structure 54. The end effector 51 is typically manipulated in pitch and yaw directions by the wrist structure 54 and, when the end effector 51 is scissors or a grasper, for example, the end effector also may be opened or closed. Using a material such as silicone at the end of the tool cover 1, i.e., for the tip cover portion 2, provides sufficient flexibility to enable the desired range of motion and overall manipulation of the end effector 51, e.g., without permanently deforming and/or otherwise tearing or damaging the tool cover 1. In various exemplary embodiments, the first material can have a durometer ranging from about 30 Shore A to about 90 Shore A. The tip cover portion 2 also is flexible enough to maintain proper coverage over the end effector 51 (e.g., over at least a portion thereof) when the end effector 51 is moved. In addition, a material such as silicone, for example, is able to both flex when the end effector is opened and is able to be reformed after the end effector is closed. This can prevent undesirable stretching and/or permanent deformation of the tip cover portion 2, which can lead to an improper fit of the tool cover 1 on the instrument and/or the tool cover 1 coming off the instrument.

Although the material, such as silicone, from which the tip cover portion 1 is formed in this embodiment is desirable to achieve the various design constraints discussed above, the inventors discovered that providing an additional material layered with the first material of the tip cover portion enables the tool cover to meet various other design constraints and improve overall performance. Thus, in various exemplary embodiments of the tool cover, a second material with a higher tear strength, for example, higher than silicone, a higher degree of toughness, a higher tensile strength, and/or a greater resistance to fracture, is used to avoid and/or minimize the risk of piercing, tearing, and/or otherwise damaging, the tool cover, for example, via collisions, back-driving the wrist (particularly without straightening the wrist first) to withdraw the instrument from the cannula, and broken cable strands that have small fibers which can push through or abrade the inside of the tip cover. Thus, in accordance with various exemplary embodiments, the base cover portion 3 is composed of a second material with a higher tear strength, a higher tensile strength and a greater ability to withstand fracture than the first material that forms the tip cover portion 2. In various exemplary embodiments, the tear strength of the first material may range from about 32 kN/m to about 60 kN/m, for example, about 41.7 kN/m, and the tear strength of the second material may range from about 60 kN/m to about 160 kN/m, for example, about 100 kN/m. In various exemplary embodiments, the tensile strength of the first material ranges from about 800 psi to about 1800 psi, for example, about 1111 psi, and the tensile strength of the second material ranges from about 5000 psi to about 7000 psi, for example, about 5850 psi. In various exemplary embodiments, a ratio of the tensile strength of the second material to the tensile strength of the first material is at least 2:1. In various exemplary embodiments, the base cover portion 3 may be composed of material having a durometer indicating hardness ranging from about 50 Shore A to about 110 Shore A, for example, about 90 Shore A, while the tip cover portion material may be composed of material having a durometer ranging from about 30 Shore A to about 90 Shore A, for example, about 80 Shore A.

When discussing the various material properties above for the first and second materials, it is noted that these are properties of the materials in a pre-processed state, that is, before any processing occurs to form the materials into the composite tool cover structure, or tip cover and base cover parts thereof.

In various exemplary embodiments, the base cover portion 3 is composed of a polyurethane, which may be a thermoplastic urethane, such as Pellethane®, for example, e.g., Lubrizol Pellethane 2363-90A. In addition to silicone providing high arc track resistance, a thermoplastic urethane, such as Pellethane®, for example, may also provide high arc track resistance. As will be described below, the combination of the first and second materials (e.g, silicone and the thermoplastic urethane) provides the benefits of flexibility, electrically insulative properties and increased tear and tensile strength, which provides increased toughness in the area in which the materials overlap.

As described above, the electrosurgical tool cover 1 is a composite structure comprising a tip cover portion 2 and a base cover portion 3, wherein the tip cover portion 2 is made with a first material (e.g., silicone) and the base cover portion 3 is made with a second material (e.g., a thermoplastic urethane such as Pellethane®). The second material properties differ from the first material properties in order to reinforce the overall structure of the electrosurgical tool cover 1.

Figure 2A:
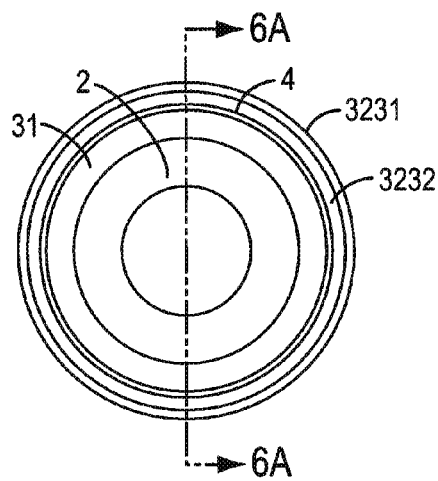
FIGS. 2A and 2B respectively show back and front end views, taken from the perspective of the embodiment illustrated in FIG. 3A, of the exemplary electrosurgical tool cover of FIGS. 1A and 1B.
Figure 2B:
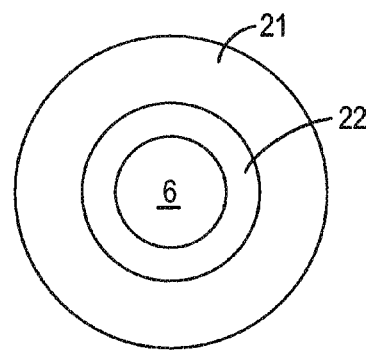
Figure 3B:
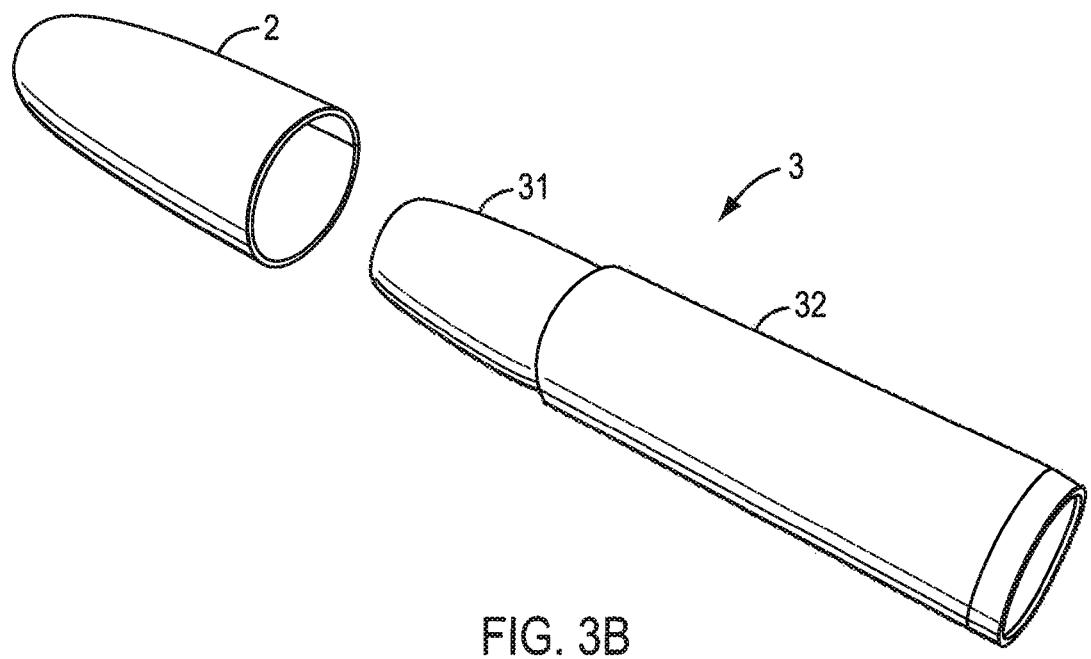

FIGS. 3A and 3B show an exploded side view and a perspective view of the composite electrosurgical tool cover 1, and FIGS. 2A and 2B show a back view (i.e., looking from the proximal end of the tool cover 1 in FIG. 3A) and a front view (i.e., looking from the distal end of the tool cover in FIG. 3A). As shown, the tool cover 1 includes a tip cover portion 2 having a generally tapered hollow body, and a base cover portion 3 comprising a generally tapered base cover portion distal part 31 and a base cover portion proximal part 32. In one exemplary embodiment, the base cover portion proximal part 32 can be generally cylindrical, although other configurations are envisioned and may depend on the configuration of the electrosurgical instrument with which the tool cover is intended to engage. The base cover portion distal part 31 and the base cover portion proximal part 32 can be a single, continuous structure made of the same second material mentioned above. In various exemplary embodiments, the base cover portion proximal part 32 may be formed as a flexible socklike structure that is positionable onto the electrosurgical instrument 5 to maintain the tool cover 1 on the electrosurgical instrument 5.

The inner surface of the base cover portion proximal part 32 is tapered at the base proximal end portion 3232 (see FIG. 6A) to receive the shaft of the electrosurgical instrument 5. The outer surface of the base cover portion distal part 31 is tapered to receive the tip cover portion 2. As will be described further below, the inner surface of the proximal end of the tip cover portion 2 may be tapered to join with the base cover portion 3.

Figure 4A:
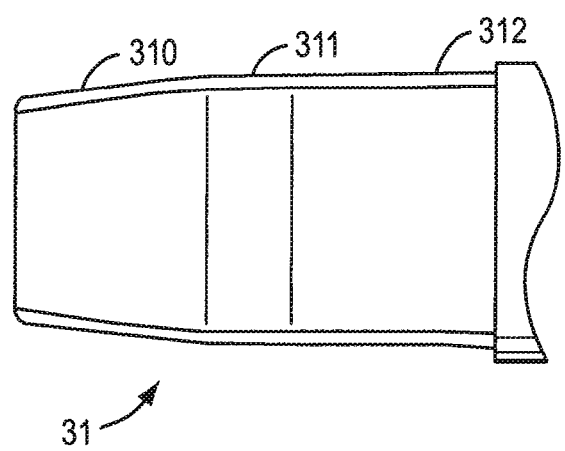
FIGS. 4A and 4B show cross-sectional views of a distal end portion and a proximal end portion, respectively, of the electrosurgical tool base cover portion shown in FIG. 3A.

The base cover portion distal part 31, as shown in FIG. 4A, comprises a hollow generally tapered structure that includes a tapered tip end portion 310, a middle body portion 311, and a bottom end portion 312. The bottom end portion 312 has a generally cylindrical shape and forms a continuous, single piece structure (which may be made via molding, for example) with the base cover portion proximal part 32. The middle body portion 311 is positioned between the bottom end portion 312 and the tip end portion 310. The tip end portion 310 has a generally tapered shape with a diameter (outer and inner) that decreases from the diameter of the middle body portion 311 in a direction away from the middle body portion 311 and therefore the diameter along the tip end portion 310 is less than the diameters of the middle body portion 311 and the bottom end portion 312.

Figure 4B:
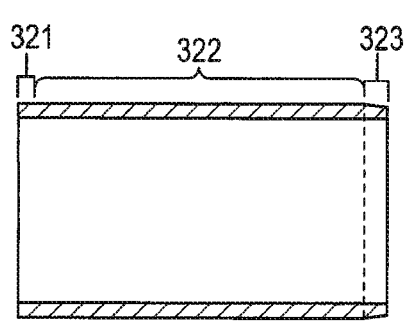

FIG. 4B shows the base cover portion proximal part 32 comprising a tip portion 321, a middle body portion 322, and a bottom end portion 323. The base cover portion proximal part 32 extends from the base cover portion distal part 31, with the tip portion 321 of the base cover portion proximal part 32 connecting with the bottom end portion 312 of the base cover portion distal part 31. The base cover portion proximal part's 32 wall thickness, inner diameter, and outer diameter is substantially the same from the tip portion 321 along the middle body portion 322 until reaching the bottom end portion 323. At the bottom end portion 323, the bottom end portion's 323 outer diameter decreases while the bottom end portion's 323 inner diameter remains the same. The change in the bottom end portion's 323 outer diameter results in a change (decrease) of wall thickness, and outer surface tapering, at the bottom end portion 323.

Figure 6A:
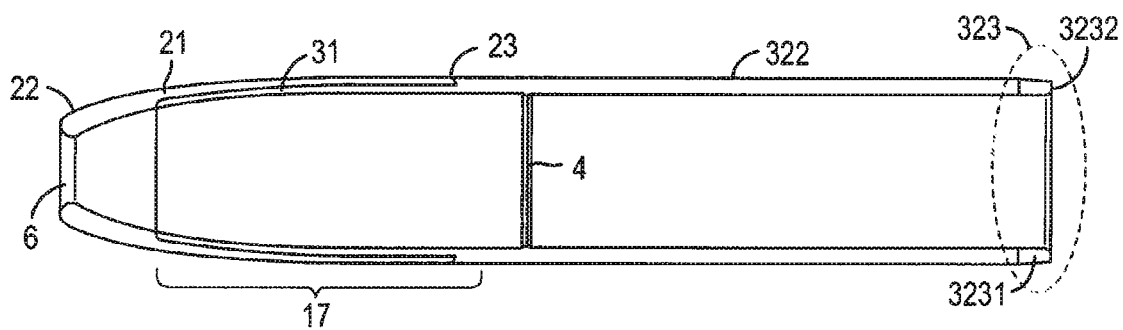
FIGS. 6A and 6B show cross-sectional and perspective cross-sectional, interior views of the electrosurgical tool cover taken from the view of 6-6 of FIG. 2A according to at least one embodiment.

As shown in FIG. 6A, for example, the bottom end portion 323 of the base cover portion proximal part 32 comprises a tapered portion 3231 and a base proximal end 3232, where the bottom end portion's 323 outer diameter is reduced by the tapered portion 3231 which extends from the middle body portion 322 of the base cover portion proximal part 32 to the base proximal end 3232. By providing the tapered portion 3231, there is no edge for the cannula to catch on during instrument removal. In an exemplary embodiment, the outer diameter at the bottom end portion 323 of the base cover portion proximal part 32 can range from about 7.6 mm to about 13 mm, while the outer diameter of the middle body portion 322 can also range from about 7.6 mm to about 13 mm.

As illustrated in FIGS. 2A and 6A, the inner surface of the middle body portion 322 of the base cover portion proximal part 32 defines a radial protrusion 4 disposed just proximal to a location where the base cover portion 3 begins to taper toward the tip cover portion 2. Further details regarding the protrusion 4 are explained below.

Figure 5A:
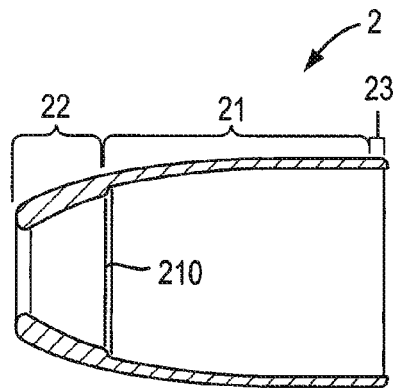
FIGS. 5A and 5B show cross-sectional and perspective cross-sectional views of the electrosurgical tool tip cover portion of FIG. 3A.
Figure 5B:
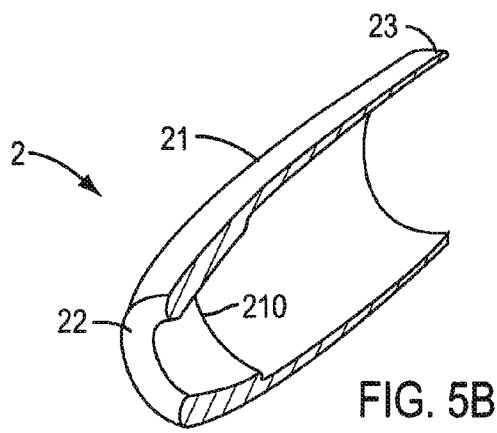

As shown in FIGS. 5A and 5B, the tip cover portion 2, which substantially surrounds and is integrally connected with the base cover portion distal part 31 (see FIG. 6A), has a generally tapered shape having a tip cover portion distal part 22, a tip cover portion main body 21, and a tip cover portion proximal part 23. FIGS. 5A and 5B show the tip cover portion 2 further comprising a recessed ledge 210 located where the inner wall of the tip cover portion 2 reduces in thickness from the tip cover portion distal part 22 to the tip cover portion's main body 21. This change in thickness results in increasing the inner diameter of the tip cover portion 2 along the tip cover portion main body 21 and the tip cover portion proximal part 23, such that the base cover portion distal part 31 is able to be connected with the tip cover portion main body 21 and the tip cover portion proximal part 23. An overlap region 17 is created where the tapered base cover portion distal part 31 connects with the tip cover portion main body 21 and the tip cover portion proximal part 23, as shown in FIG. 6A, in which the composite, multi-layered structure combines the properties of the electrosurgical tip cover's 2 first material with the base cover portion's 3 second material. The result of the combination is a reinforced composite structure, in which properties such as arc track resistance and high dielectric strength, in comparison with a tool cover made of a single material, such as silicone, are at a minimum maintained and durability is increased without compromising the electrosurgical tool cover 1 range of motion.

Referring now to FIGS. 6A through 7B, further cross-sectional side and perspective views of the electrosurgical tool cover 1 are illustrated and show the tip cover portion 2 and the base cover portion 3 integrally attached together to form a single composite structure. In various exemplary embodiments, the integral attachment of these two portions is achieved by overmolding, in which the combination of a layer of the tip cover portion 2 and a layer of the base cover portion 3, each made of different materials, results in a composite structure. Additional details regarding an exemplary technique for making an electrosurgical tool cover via overmolding in accordance with various exemplary embodiments are described further below. However, those having ordinary skill in the art will appreciate that other techniques for integrally attaching the tip cover portion 2 with the base cover portion 3 can be used.

As depicted in FIGS. 6A-7B, the tip cover portion distal end 22 has the opening 6 defined therethrough, the tip cover portion main body 21 overlaps the base cover portion distal part 31 at the overlap region 17, and the middle body portion 322 of the base cover portion proximal part 32 extends away from the base cover portion distal part 31. As will be discussed further below and shown best in FIG. 6B, the tip end portion 310 of the base cover portion distal part 31 joins the tip cover portion 2 at the juncture between the tip cover portion distal part 22 and the tip cover portion main body 21.

As mentioned above, the overlap region 17 is a region that is made of the differing first and second materials layered one over the other, including the first, more flexible material with enhanced dielectric strength (electrically insulative) properties, such as silicone, surrounding the second material having a higher tear strength than the first material yet also exhibiting relatively high dielectric strength (relatively highly electrically insulative), such as, for example, a thermoplastic urethane, such as Pellethane®. As mentioned above, the composite structure of the overlap region 17 includes an inner surface of the tip cover portion 2 made of the first material, such as silicone, surrounding and integrally connected to an outer surface of the base cover portion 3 made of the second material, which may be a thermoplastic urethane such as Pellethane®. This multi-layer, composite configuration provides a material with improved impact and toughness and a relatively high tear strength at the vicinities of the electrosurgical instrument wrist member, described in more detail below, and also provides a material with superior electrical properties and elastic flexibility at the tip cover portion 2 disposed at the end effector.

As shown in FIG. 11, for example, when the electrosurgical instrument 5 is inserted into the tool cover 1 (e.g., somewhat analogous to putting a sock on), the wrist structure 54 of the electrosurgical instrument 5 is positioned within the overlap region 17, and is thus housed by both the first material of the tip cover portion 2 and the second material of the base cover portion 3. The combination of layers provides suitable flexibility for the range of motion of the electrosurgical instrument 5, more particularly to the wrist articulation, while enhancing the impact strength and durability of the electrosurgical tool cover 1.

As mentioned above, it is desirable for the second material to exhibit electrically insulative properties with higher impact and tear resistance properties as compared to the first material used for the tip cover portion 2, in order to increase the electrosurgical tool cover's 1 durability at the portion close to the wrist structure 54. The area of the tool cover 1 that is configured to surround the wrist structure 54 of the electrosurgical instrument 5 may be subject to particularly problematic issues. Due to the articulations of the wrist structure 54 or combination of wrist structure components, the tool cover 1 material may be stretched along the wrist member 54, particularly when the wrist structure 54 is rotated in the pitch or yaw direction. The second material is selected from a material such as polyurethane material (e.g., Pellethane®) which has a high abrasion and tear resistance, extremely high flex-life, and heat resistance. The second material also has a high impact strength. As mentioned above, in various exemplary embodiments, the second material has a durometer ranging from about 50 Shore A to about 110 Shore A, for example, about 90 Shore A, while the first material of the tip cover portion 2 may have a durometer ranging from about 30 Shore A to about 90 Shore A, for example, about 80 Shore A. Thus, the combined properties of the first material of the tip cover portion 2 and the second material of the base cover portion 3 protect against the tool cover 1 cracking or breaking down from multiple and varied range of motion cycles at the wrist structure 54 as it abuts against and stretches the tool cover 1.

The combined material properties also can protect against impact from other objects that come into contact and/or impact with the tool cover 1, such as, for example, other instruments, bones, etc. The overlap region 17 within which the wrist structure 54 is located when the electrosurgical instrument 5 is received within the tool cover 1 thus provides the increased tear strength by the second material, particularly due to its closer proximity to the wrist structure 54, and provides the flexibility, temperature resistance and insulative properties of the first material. Moreover, placing the tougher, second material of the base cover portion 3 on an inner portion of the tool cover 1 and thus adjacent to the electrosurgical instrument, provides a level of electrical insulative protection should the outer, less tear resistant first material forming the tip cover portion 2 tear at the wrist member 54, for example, due to the relatively high impact and stretching forces associated with that region. By maintaining the integrity of the tool cover 1, at least by virtue of the second material properties of the base cover portion, the risk of arc tracking and/or other electrical conduction through the tool cover at the wrist member is significantly reduced, but a large range of motion and maneuverability is maintained due to the presence of the more flexible overlaid first materials of the tip cover portion 2.

In addition, the combination of the first material and the second material in the overlap region 17 can overcome some of the other problems that may occur during surgical use. In particular, the tool cover 1 may become pinched by the wrist structure 54 as it is articulated and manipulated. Thus, because the second material, such as a thermoplastic urethane, e.g., Pellethane®, has a higher tear strength than the first material, the second material may be able to minimize and/or prevent the formation of holes through the tool cover 1 due to such pinching. Further, due to the stretching and flexing of the wrist structure 54 against the tool cover 1, abrasion forces may be exerted against the interior surfaces of the tool cover by the wrist structure 54. In addition, there may also be abrasion forces exerted on an outer surface of the tool cover 1, for example, due to contact of the tool cover 1 with tissue, bone, organs, other instruments during use, or with the cannula during insertion or removal. The combination of materials at the overlap region 17, specifically the use of the stronger and more tear resistant second material that is disposed adjacent to the electrosurgical instrument, can protect against tears, rips or holes through the tool cover 1 that may occur from abrasion or impact with other objects. In particular, because of its high tear strength, the second material can prevent or minimize tearing of the tool cover 1 due to the abrasion either caused by the wrist structure 54 or by structures other than the electrosurgical instrument (e.g., other instruments, bones, cannulas, etc.). Further, the higher tear strength and higher tensile strength of the second material allows the tool cover 1 to withstand fatigue, particularly at the wrist structure 54.

Including the overlap region 17 of the tool cover 1 so as to surround the wrist structure 54 when the tool cover is assembled with an electrosurgical instrument, also permits the tool cover 1 to elastically deform with, and subsequently reform after, movement (e.g., articulation) of the wrist structure 54. In particular, the materials used to form the overlap region 17 permit the tool cover 1 to fold in a desired orientation when the wrist structure 54 is manipulated, for example, to avoid jamming of the wrist structure 54 as it is articulated. Both silicone and Pellethane®, for example, exhibit sufficient elastic deformation and reformation properties of the tool cover 1.

As shown in FIG. 6A, for example, the tip cover portion 2 at the tip cover portion distal part 22 does not overlap the base cover portion 3 and accordingly is formed of only the first, more flexible material, such as, e.g., silicone. Thus, the only material at the exposed end effector 51 is the highly electrically insulative, highly temperature resistant, and more flexible first material, e.g., silicone. The tip cover portion distal part 22 can have a relatively larger wall thickness than the material at the tip cover portion main body 21 and the tip cover portion proximal part 23 because of the proximity of the tip cover portion distal part 22 to the high temperature of the exposed end effector 51. Thus, the wall thickness of the tip cover portion distal part 22, which does not overlap with the base cover portion 3, is larger than the wall thickness of the tip cover portion main body 21 and the tip cover portion proximal part 23 in the overlap region 17 because the outer diameter of the tool cover 1 must be able to work within relatively small passages, such as, e.g., cannulas. The wall thickness of the first material at the tip cover portion distal part 22 in various exemplary embodiments can range from about 0.5 mm to about 1.5 mm, for example, the thickness may be about 1.0 mm. In addition, the wall thickness at the tip cover portion distal part 22 is larger than a combined wall thickness of the first and second materials at the overlap region 17. The combined wall thickness of the first and second materials in the overlap region 17 in various exemplary embodiments can range from about 0.5 mm to about 1.5 mm, for example, the combined wall thickness in the overlap region can be about 0.5 mm. In various exemplary embodiments, the outer diameter of the tool cover 1 in the overlap region 17 may be about 7.5 mm.

Figure 6B:
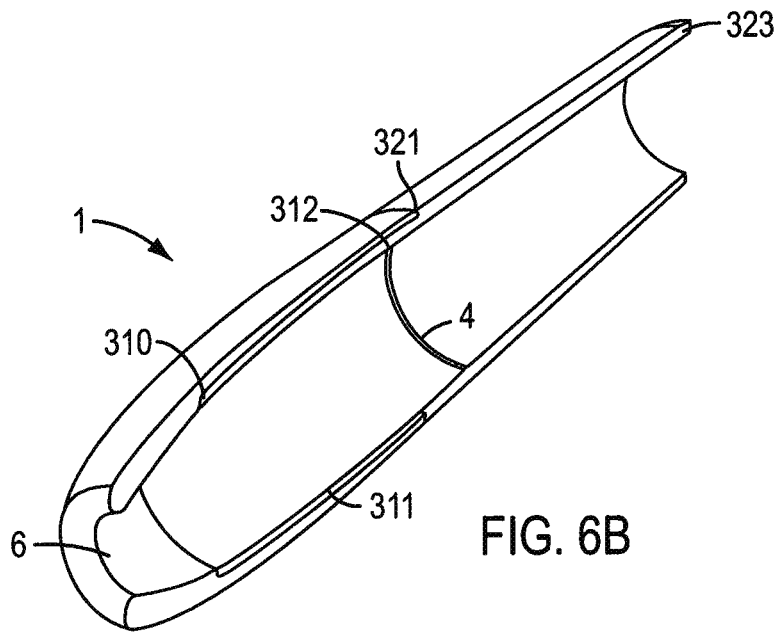
Figure 7A:
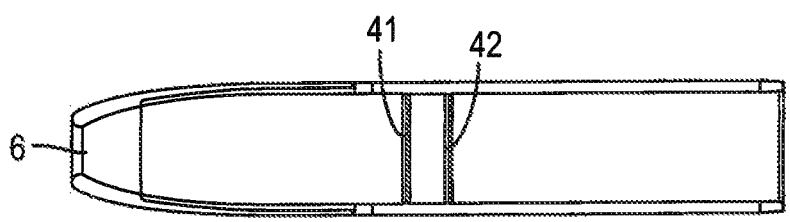
FIGS. 7A and 7B are cross-sectional and perspective cross-sectional interior views of the electrosurgical tool cover according to another exemplary embodiment.
Figure 7B:
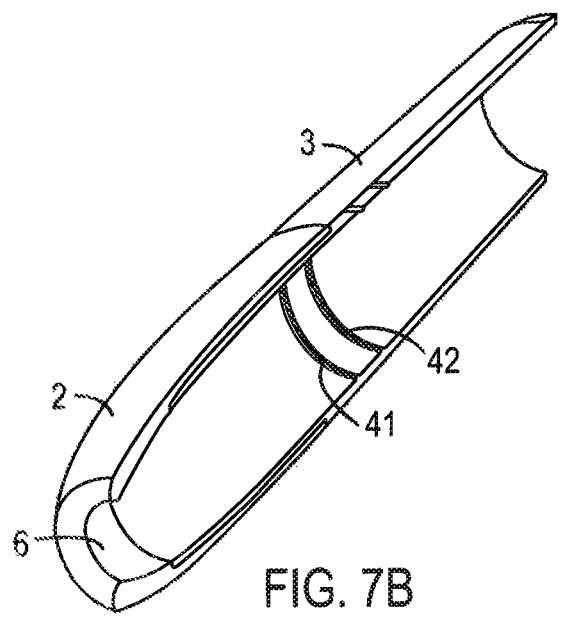

As mentioned above, and with reference now to FIGS. 6A through 7B, in various exemplary embodiments, the inner walls of the base cover portion 3 can be provided with one or more radial protrusions (e.g., 4 in the exemplary embodiment of FIGS. 6A and 6B, and 41, 42 in the exemplary embodiment of FIGS. 7A and 7B). In an exemplary embodiment, the one or more protrusions 4, 41, 42 can function as a locking mechanism and simultaneously as a seal, explained below in more detail.

Figure 8A:
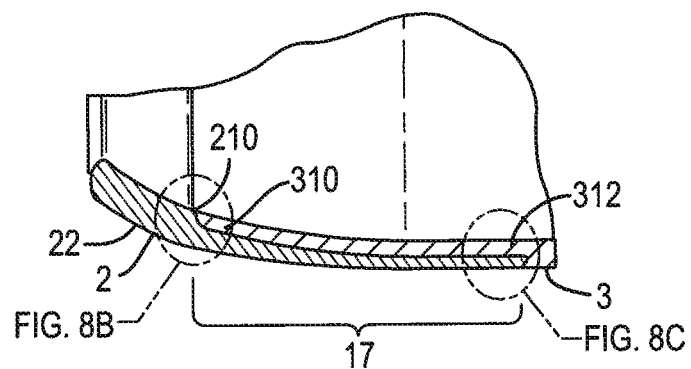
FIGS. 8A through 8C are partial cross-sectional views showing portions of the electrosurgical instrument tool cover of FIG. 4 including the tip cover portion and the overlap region according to at least one embodiment.
Figure 8B:
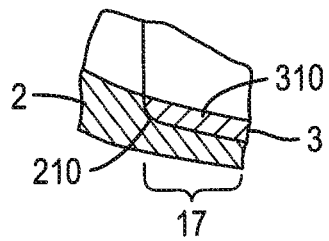
Figure 8C:
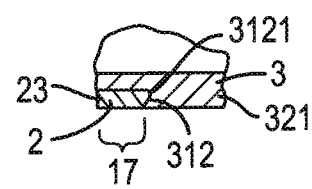

FIGS. 8A through 8C show details of portions of the electrosurgical tool cover including the overlap region 17 in which the tip cover portion 2 and the base cover portion 3 are combined to provide a composite structure. More particularly, the figures depict transitions between the tip cover portion 2 and the base cover portion 3 on either side of the overlap region 17. FIG. 8A shows a partial cross-sectional detailed view of the multi-layer structure of the overlap region 17, wherein the tip cover portion 2 surrounds the base cover portion 3, more particularly the tip cover portion's main body 21 surrounding the base cover portion distal part 31, as explained above. As shown in FIG. 8A, the structure provides two transitional locations in which the structure changes from a multi-layer section to a single layer section. The first transitional location, shown best in FIG. 8B, is located at the start of the recessed ledge 210 of the tip cover portion 2, close to the tip cover portion distal part 22. The second transitional location, shown best in FIG. 8C, is located at the tip cover portion proximal part 23, at the end of which the tool cover transitions to the single, second material of the base cover portion 3.

The detailed view of FIG. 8B illustrates the transition between the tip cover portion 2 and the base cover portion distal part's 31 tip end portion 310. The tip end portion 310 of the base cover portion distal part 31 is shaped to have a smooth surface at the transitional location, such as a curved surface, instead of a sharp edged surface, in order to avoid damage at the point of connection between the tip cover portion 2 and the base cover portion 3. The curved surface provides a smooth surface for the region of contact between the tip end portion 310 of the base cover portion distal part 31 and the tip cover portion distal part 22. This large contact region enables the stress at the point of connection to be distributed over a larger area than, for example, a butt joint would provide. The larger bond area, which is due to the increased length along which the first material of the tip cover portion 2 is bonded to the second material of the tip end portion 310 of the base cover portion 3, therefore can reduce the risk of ruptures or disengagement at the area of close contact between the tip end portion 310 of the base cover portion distal part 31 and the tip cover portion distal part 22, particularly after continuous motion or articulation of the electrosurgical instrument wrist structure 54 housed in that region. In particular, when the first material is overmolded onto the second material, there is a greater bond strength than, for example, a butt joint between the materials would provide, thus decreasing the risk of the materials separating from one another at this juncture. In addition, butt joints can cause stress concentrations, and thus the transitional location having the gradually tapered construction provides for less stress concentrations at the joined area.

The second transitional location is located at the base cover portion distal part's 31 bottom end portion 312 and the tip cover portion proximal part 23, close to the tip portion 321 of the base cover portion proximal part 32. FIG. 8C shows a detailed view of the second transitional location, in which the tip cover portion proximal part 23 is received in a curved-in structure 3121 at the bottom end 312 of the base cover portion distal part 31 and the tip portion 321 of the base cover portion proximal part 32. The bottom end 312 may be angled to be less than 90 degrees with respect to the outer wall surface in order to increase the bond strength between the first and second materials by interlocking the materials together at this transitional location. The angled bottom end 312 may provide a greater bonded area between the material of the tip cover portion proximal part 23 and the material of the base cover portion proximal part 32 at the transitional point than, for example, a butt joint between the two materials.

The material of the tip cover portion proximal part 23 ends at the tip portion 321 of the base cover portion proximal part 32, which defines an end of the overlap region 17. The base cover portion proximal part 32 is composed of only the second material. The materials do not overlap in the portion of the tool cover 1 extending proximally from the second transitional location. In various exemplary embodiments, the base cover portion proximal part 32 can have a wall thickness of the second material ranging from about 0.5 mm to about 1.5 mm. The base cover portion proximal part 32 can have an inner diameter ranging from about 5.0 mm to about 7.6 mm, for example, about 7 mm, in various exemplary embodiments. The outer diameter of the tool cover 1 at the base cover portion proximal part 32 can range from about 5.0 mm to about 7.6 mm, for example, about 7.52 mm, in order to fit within existing cannulas having an inner diameter larger than the outer diameter of the tool cover 1.

The curved structure of the tip cover portion proximal part 23 in relation to the tip portion 321 of the base cover portion proximal part 32 also provides greater bonding between the first and second materials at the second transitional location than, for example, a butt joint would provide, and assists in holding the electrosurgical tip cover portion 2 in place to avoid disengagement from the base cover portion 3.

Figure 9A:
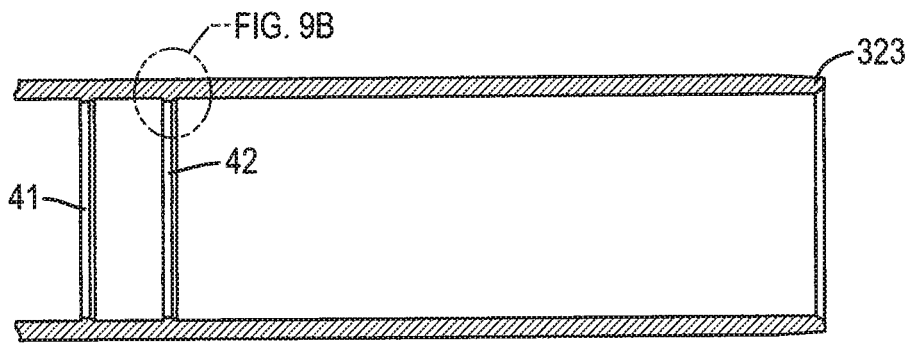
FIG. 9A is a partial cross-sectional view of the base cover portion of FIG. 3A.
Figure 9B:
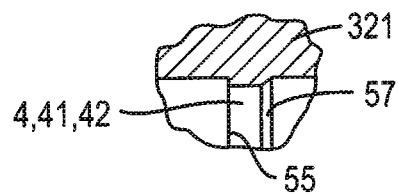
FIG. 9B is a detailed view of a section of the base cover portion of FIG. 9A.

The protrusions 4, 41, 42 as shown in a cross-sectional view in FIG. 9A, with a single protrusion configuration being exemplified in the cross-sectional detailed view FIG. 9B, can be located on the inner wall of base cover portion 3 and protrude inwardly toward the center of the base cover portion 3 to reduce the inner diameter of the electrosurgical base cover portion 3 at the location of the one or more protrusions 4, 41, 42. Protrusions 4, 41, 42, as mentioned above, are configured to press against the outer surface of the electrosurgical instrument 5 to form a liquid seal that prevents liquid from entering into undesired compartments along the electrosurgical instrument 5, which could potentially cause undesired electrical conductions to the back end of the instrument 5. The second material used in the electrosurgical base cover portion 3, such as Pellethane®, can permit the effective formation of the protrusions 4, 41, 42 via molding (including overmolding), for example.

The sealing may also be achieved by using one or more radial recesses (as shown and discussed below with reference to FIG. 11) instead of protrusions 4, 41, 42. Such recesses may be configured to receive one or more sealing ribs and/or other sealing structures (e.g., O-rings, etc.) provided on an outer surface of the electrosurgical instrument. When a protrusion is used, the protrusion 4, 41, 42 is configured to have a flat portion 55 and a tapered portion 57 (shown best in FIG. 9B), where the tapered portion 57 of the protrusion 4 is tapered toward the base cover portion 3 inner wall. This configuration can facilitate installation of the electrosurgical tool cover 1. The tapered portion 57 of the protrusion 4 helps to allow the protrusion 4, 41, 42 to ramp up and over a mating feature on the electrosurgical instrument. The flat portion 55, which extends perpendicularly to the base cover portion 3 inner wall, prevents the electrosurgical tool cover 1 from inadvertently falling off of the instrument 5. A more detailed description of the electrosurgical tool cover 1 installation on an electrosurgical instrument is set forth below.

Figure 10:
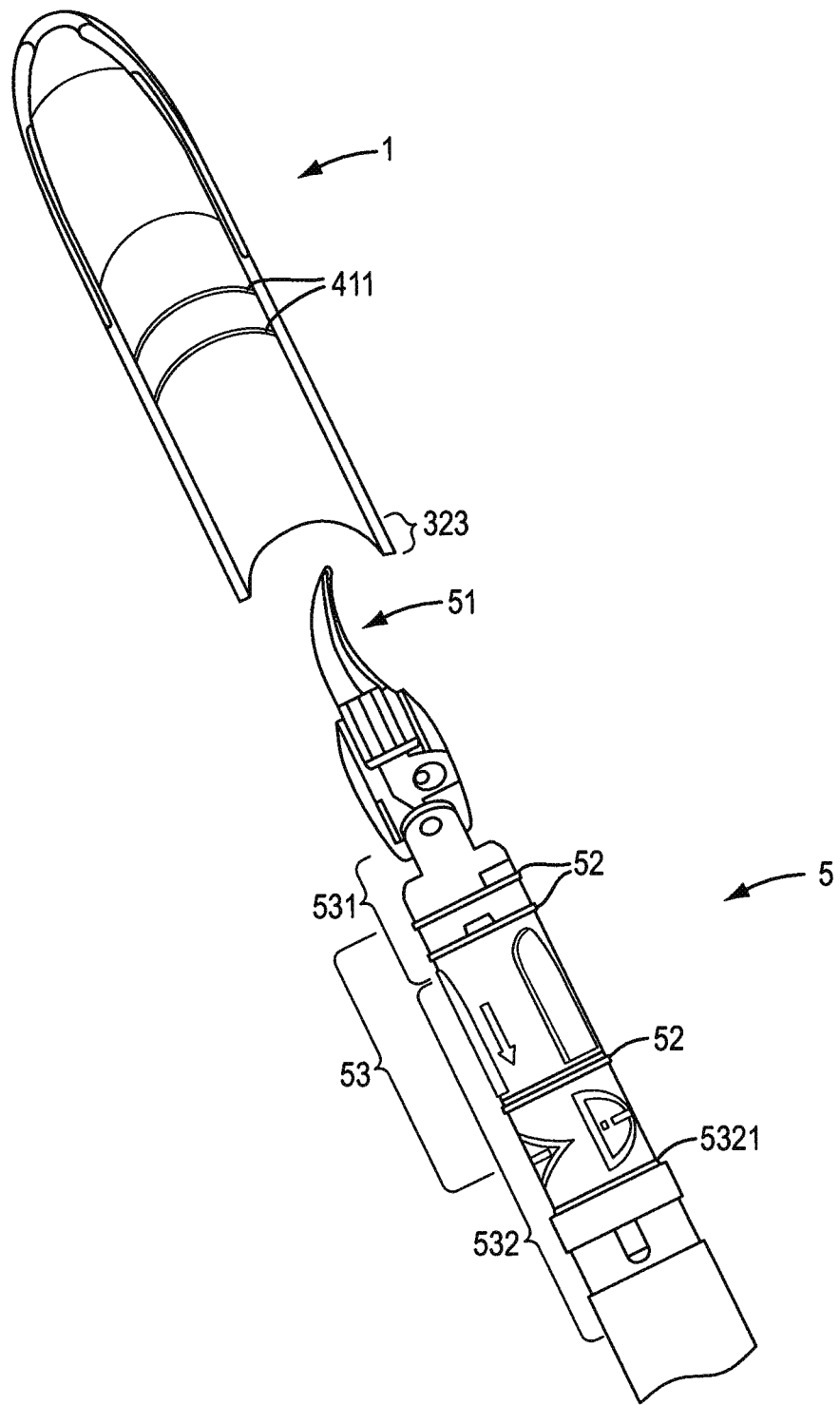
FIG. 10 is a perspective cross-sectional view of the electrosurgical tool cover and a partial perspective view of the electrosurgical instrument during installation of the cover on the instrument.

FIG. 10 shows an exemplary electrosurgical instrument 5 including an elongate shaft 53 having an instrument proximal end (not shown), an instrument distal end 531 and an instrument main body 532 which in an exemplary embodiment can include at least one protrusion or sealing rib 52 (though two sealing ribs are depicted in FIG. 10) on an outer surface thereof. When such sealing ribs are provided, they can be configured to engage with one or more corresponding recesses (described above and below) provided on the inner wall of the tool cover to provide a sealing and securing function. A wrist structure 54 (seen more clearly in FIG. 11) is disposed at the distal end 531 of the shaft 53. An electrocautery end effector 51 is mounted to the wrist structure 54. An interface (not shown) is disposed at the proximal end of the shaft 53. An electrical conductor extends from the interface to the end effector 51 so as to deliver electrical energy through the electrosurgical instrument 1 and to tissue engaged by the end effector 51.

As shown in FIGS. 10 and 11, the base cover portion 3 facilitates installation of the electrosurgical tool cover 1 on the electrosurgical instrument 5 by sliding movement onto the tool cover 1, analogous to sliding a sock onto an appendage. More particularly, the bottom end portion 323 of the base cover portion proximal part 32 is caused to stop on a shaft flange 5321 of the surgical instrument 5. The base cover portion 3 includes recesses 411 on an inner wall thereof, which receive the ribs 52 of the electrosurgical instrument 5. The recesses 411 and ribs 52 are configured to serve as a liquid sealing mechanism for the surgical instrument, as explained above. The radial recesses 411 mate with the ribs 52 at several points respectively so that the electrosurgical tool cover 1 is sufficiently retained over the instrument 5 and does not inadvertently fall off during surgery. Alternately, the base cover portion 3 could be retained over the instrument utilizing interlocking snap features or other securing mechanisms. In another embodiment, the inner surfaces of the tool cover 1 does not include recesses 411, for example, and hoop strength of the tool cover 1 and the friction of the ribs 52 on the electrosurgical instrument 5 in relation to the smooth inner surface of the tip cover 1 retains the tool cover 1 on the electrosurgical instrument 5.

As shown in FIG. 11, the electrosurgical tool cover 1 is installed partially over the end effector 51, over the wrist structure 54 and over a distal end of the elongate shaft 53 so as to inhibit conduction of electrical current from the electrosurgical instrument to the patient's tissues at undesired/unintended locations along electrosurgical instrument 5 to prevent patient injuries during use. Rather, the electrosurgical tool cover 1 is designed so that when it is installed properly in place, electrical current can only be conducted to tissues through the exposed end effector, for example, to promote blood coagulation during usage (e.g., cutting, shearing, etc.), ablation, and/or other cautery-based procedure, and not to other parts of the patient's body.

FIG. 12 through FIG. 21B show an electrosurgical tool cover according to another exemplary embodiment. The following description of this exemplary embodiment will mainly focus on some of the different features found in the embodiment of the tool cover 10 of FIGS. 12-21B. Similar to the example of the first embodiment of the electrosurgical tool cover 1, the exemplary embodiment of the electrosurgical tool cover 10 is reinforced by providing a composite structure comprising multiple layers of materials having properties that withstand high temperatures associated with cautery procedures, and arc tracking, and exhibit high dielectric strength. As with the electrosurgical tool cover 1, the electrosurgical tool cover 10 includes a composite reinforced insulation cover including a tip cover portion 8 made of a first material and a base cover portion 9 made of a second material, the first material having an ability to withstand high temperatures and provide a high electrically insulative property, the second material having a high toughness, higher tear strength, higher tensile strength and thus a higher ability to withstand impact and withstand fracture, as well as sufficiently high electrically insulative properties, where the composite structure is flexible. FIG. 12 shows a side view of the tool cover 10 which shows a hollow base cover portion 9 integrally connected to the tip cover portion 8.

The materials used to form the tool covers in the first embodiment and in the second embodiment can be the same. Thus, in various exemplary embodiments, the tear strength of the first material may range from about 32 kN/m to about 60 kN/m, for example, the tear strength of the first material can be about 41.7 kN/m, and the tear strength of the second material may range from about 60 kN/m to about 160 kN/m, for example, the tear strength of the second material can be about 100 kN/m. In various exemplary embodiments, the tensile strength of the first material may range from about 800 psi to about 1800 psi, for example, about 1111 psi, and the tensile strength of the second material may range from about 5000 psi to about 7000 psi, for example, about 5850 psi. In various exemplary embodiments, a ratio of the tensile strength of the second material to the tensile strength of the first material should be at least 2:1. In various exemplary embodiments, the base cover portion 3 may be composed of a material having a durometer indicating hardness ranging from about 50 Shore A to about 110 Shore A, for example, about 90 Shore A, while the tip cover portion material may be composed of material having a durometer ranging from about 30 Shore A to about 90 Shore A, for example, about 80 Shore A.

As above, the various material properties above for the first and second materials correspond to properties of the materials in a pre-processed state, that is, before any processing occurs to form the materials into the composite tool cover structure, or tip cover and base cover parts thereof.

Figure 13:
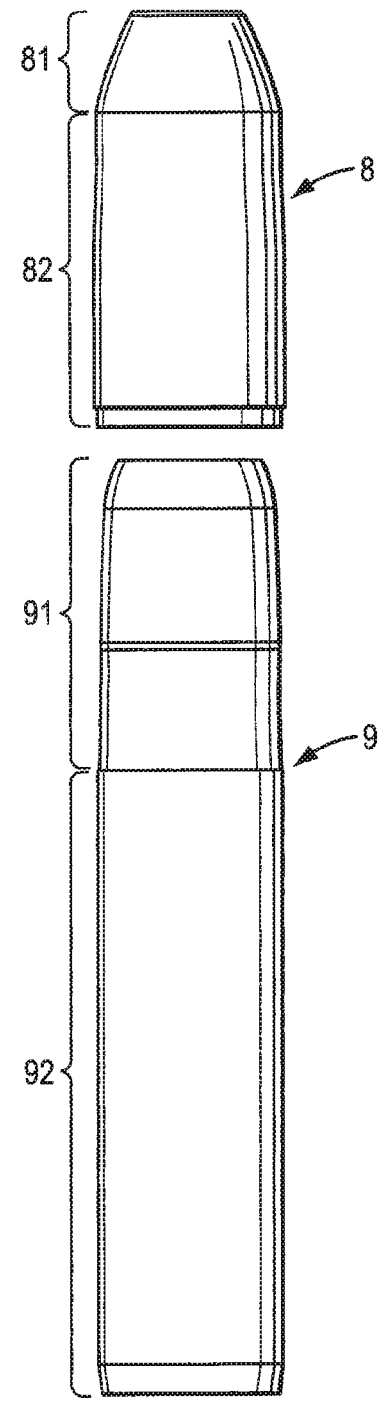
FIG. 13 is an exploded side view of the electrosurgical tool cover of FIG. 12 showing principal parts thereof.

FIG. 13 is an exploded view of the electrosurgical tool cover 10 showing the electrosurgical tip cover portion 8 made of a first material (such as, e.g., silicone), as described with reference to the description of the tool cover 1, and including a tip cover portion proximal part 82 that extends towards a tip cover portion distal part 81 having a generally tapered hollow body. As further shown in FIG. 13, the base cover portion 9 includes a generally tapered base cover portion distal part 91 and a base cover portion proximal part 92 formed of a second material (such as, e.g., a polyurethane, e.g., Pellethane®), as described above with reference to the tool cover 1.

Figure 14A:
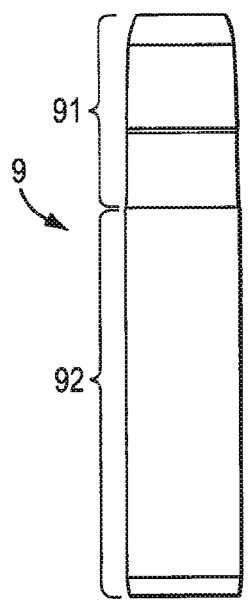
FIGS. 14A and 14B show side and cross-sectional views of the electrosurgical tool base cover portion of FIG. 13.
Figure 14B:
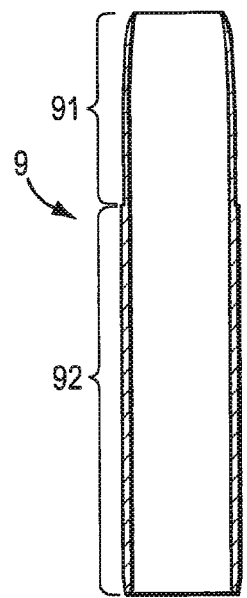

The base cover portion proximal part 92, as shown in FIGS. 14A through 14B, extends from the base cover portion distal part 91. The wall thickness of the base cover portion distal part 91 is reduced in comparison to the wall thickness of the base cover portion proximal part 92, as shown in FIG. 14B. In various exemplary embodiments, the wall thickness of the base cover portion proximal part 92 can range from about 5.0 mm to about 7.6 mm, and the wall thickness of the base cover portion distal part 91 can range from about 5.0 mm to about 7.6 mm.

Figure 15:
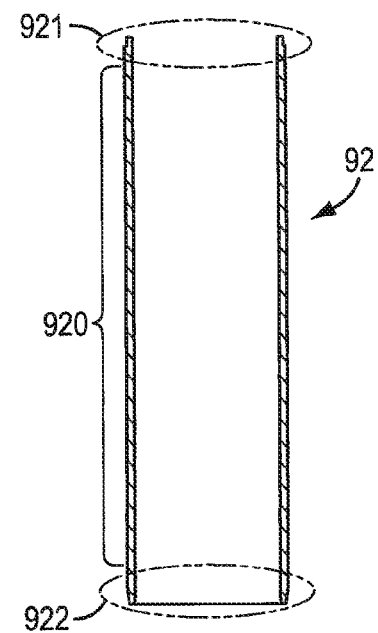
FIG. 15 shows a partial cross-sectional side view of the base cover portion of FIG. 13, more particularly the base cover portion proximal part.

FIG. 15 shows the base cover portion proximal part 92 comprising a tip portion 921, a middle body portion 920 and a bottom end portion 922. The base cover portion proximal part's 92 thickness, inner diameter and outer diameter is substantially the same from the tip portion 921 to the middle body portion 920 until reaching the bottom end portion 922. At the bottom end portion 922, the bottom end portion's 922 outer diameter decreases while the bottom end portion's 922 inner diameter remains the same. The change in diameter results in a change in wall thickness of the bottom end portion 922. The bottom end portion 922 comprises a tapered portion wherein the bottom end portion's 922 outer diameter is reduced by the tapered portion. This configuration is similar to that described with reference to the tool cover 1 described above, and the tapered portion prevents the cannula from catching an edge of the tool cover 10.

Figure 16A:
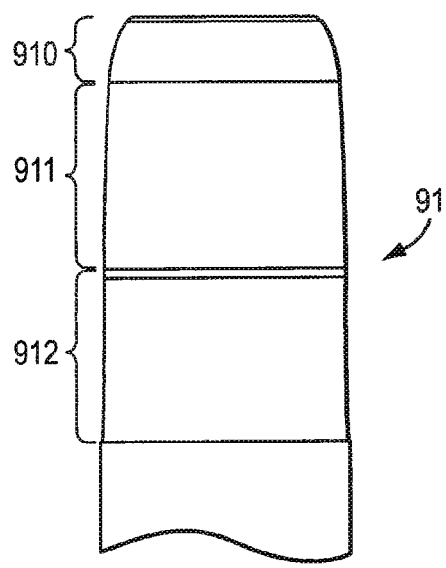
FIGS. 16A and 16B show side and cross-sectional views of the base cover portion distal part of FIG. 13.
Figure 16B:
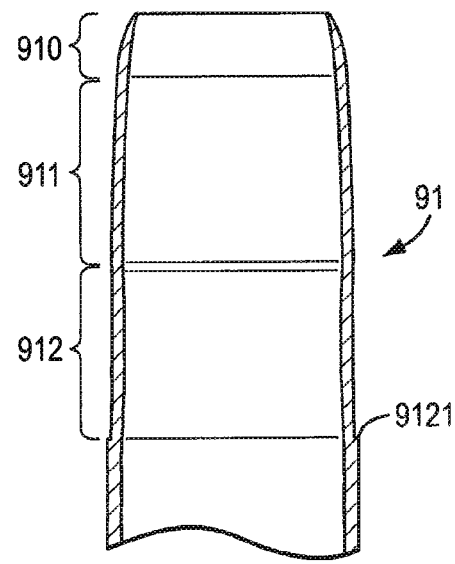

FIGS. 16A and 16B are directed to the base cover portion distal part 91. The base cover portion distal part 91 comprises a hollow generally tapered structure including a tapered tip end portion 910, a middle body portion 911 and a bottom end portion 912. The bottom end portion 912 has a generally cylindrical shape and forms a continuous, single piece structure (which may be made via molding, for example) with the base cover portion proximal part 92. The middle body portion 911 is positioned between the bottom end portion 912 and the tip end portion 910. The tip end portion 910 has a generated tapered shape with a diameter (outer and inner) that decreases from the diameter of the middle body portion 911 in a direction away from the middle body portion 911 and therefore the diameter along the tip end portion 910 is less than the diameters of the middle body portion 911 and the bottom end portion 912. The bottom end portion 912 curves slightly inward at a central region thereof. The reduction in diameter of the base cover portion distal part 91 creates a flange 9121 between the bottom end portion 912 and the base cover portion proximal part 92. The middle elongated body portion 911, positioned between the bottom end portion 912 and the tip end portion 910, has a bigger outer diameter than the bottom end portion 912.

Figure 17A:
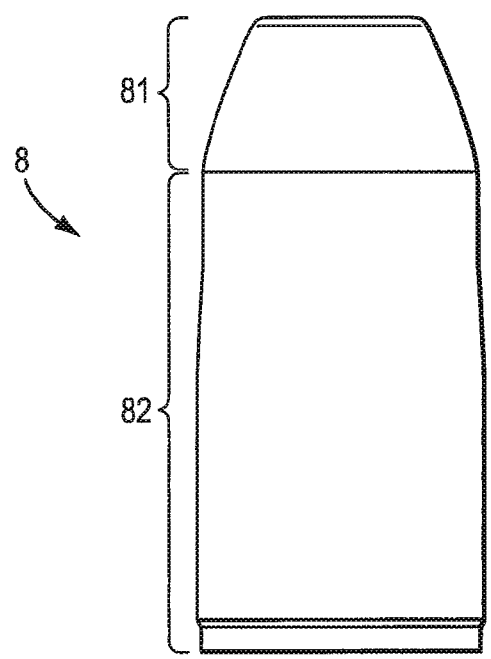
FIGS. 17A and 17B show front and cross-sectional views of the tip cover portion of FIG. 13.
Figure 17B:
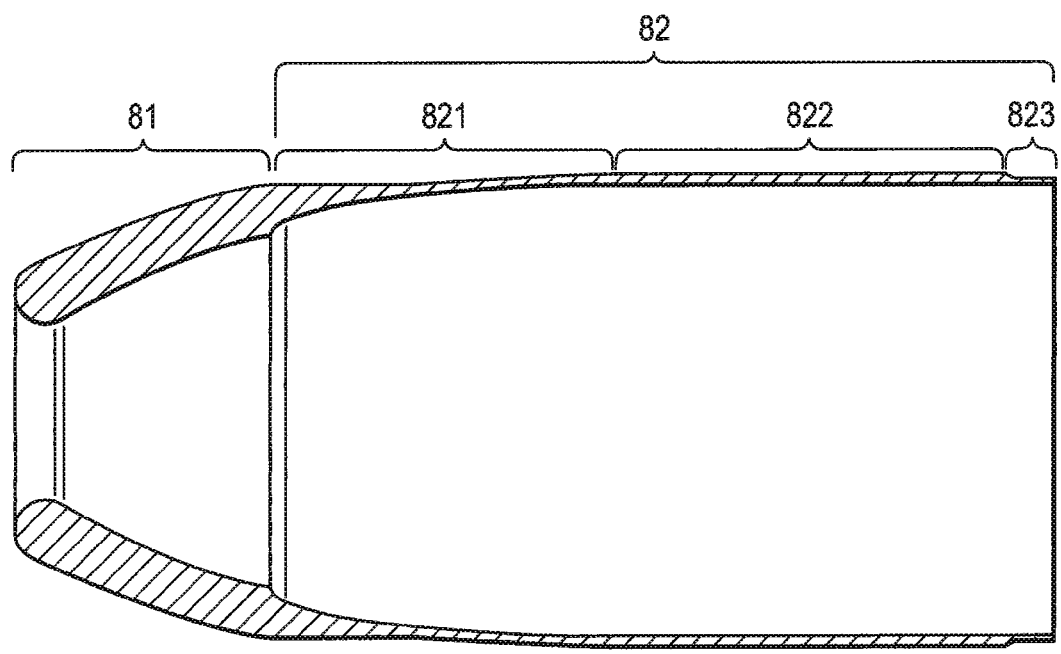

As shown in FIGS. 17A and 17B, the tip cover portion 8, as mentioned, comprises a tip cover portion proximal part 82 and a tip cover portion distal part 81. The tip cover portion proximal part 82 is divided in a first section 821, a second section 822, and a third section 823. The first section 821 is attached to the tip cover portion distal part 81. The tip cover portion proximal part's 82 outer diameter remains the same until reaching the third section 823, wherein a diameter reduction is attained. A recess 812 (see FIG. 19A) located at the tip cover portion's 8 inner walls extend from the tip cover portion distal part 81 toward the third section 823, more particularly through the tip cover portion's first section 821 toward the tip cover portion's third section 823. The thickness of the material at the tip cover portion distal part 81, which is mainly the part in contact with the end effector 51, is substantially increased in relation to the thickness of the material at the first, second and third sections 821-823 of the tip cover portion 8, as shown in FIG. 17B, in order to sustain higher temperatures.

Figure 18A:
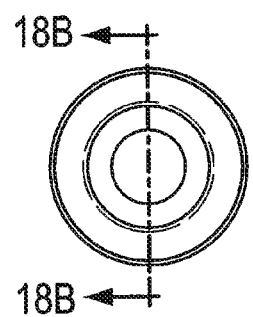
FIG. 18A is a front view of the electrosurgical tool over of FIG. 12.
Figure 18B:
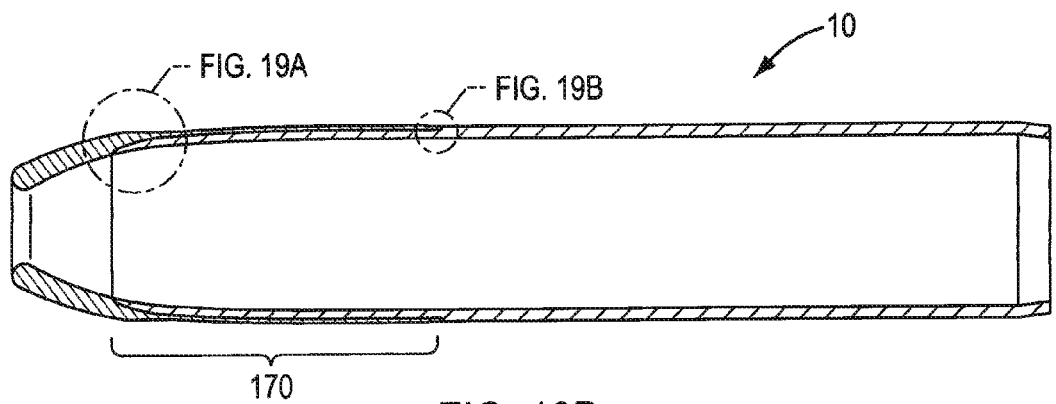
FIG. 18B is a side cross-sectional view taken along line 18B-18B of the electrosurgical tool cover of FIG. 12.

FIG. 18A provides a front view of the electrosurgical tool cover 10 illustrated in FIG. 12, and FIG. 18B illustrates a cross-sectional view of the electrosurgical tool cover 10 taken along line 18B-18B of FIG. 18A, wherein the tip cover portion 8 and the base cover portion 9 are coupled together. The coupling of these two portions can be formed by, for example, but not limited to, overmolding wherein the combination of a layer of the electrosurgical tip cover portion 8 and a layer of the electrosurgical base cover portion 9 made of differing materials are overlapped, in an overlap region 170 (similar to overlap region 17 with differences being discussed further below) resulting in an integrally connected, multi-layer, composite structure. The tip cover portion distal part 81 does not overlap with the base cover portion 9. Thus, the tip cover portion distal part 81, which receives the end effector 51 of the electrosurgical instrument 5, is composed of only the first material, which may be silicone, for example. The first material has the ability to withstand extremely high temperatures, such as for example, associated with the arc coming from a cautery end effector (e.g., greater than 1000° F.) to those associated with the boiling temperatures of liquid such as blood and/or saline (e.g., about 212° F. to about 220° F.) and has greater insulatory qualities than the second material, and thus by providing only the first material at the tip cover portion distal part 81, the area closest to the high temperature and in need of the material with greater flexibility and temperature resistance is protected by the first material of the tip cover portion 8. In addition, as shown in FIG. 18B, for example, a wall thickness of the overlap region 170 is larger than a wall thickness of the base cover portion proximal part

92. In various exemplary embodiments, the wall thickness of the overlap region 170 ranges from about 0.5 mm to about 1.5 mm, for example, about 0.5 mm, and the outer diameter of the tool cover 10 at the overlap region 170 may be about 7.5 mm, for example. The wall thickness of the base cover portion proximal part 92 may, in various exemplary embodiments, range from about 0.5 mm to about 1.5 mm, for example, the thickness may be about 0.5 mm.

Figure 18C:
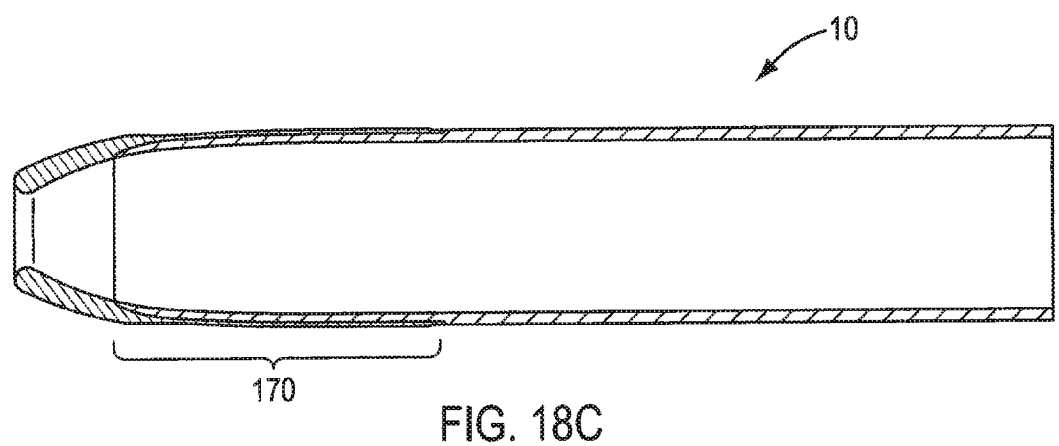
FIG. 18C is a view similar to FIG. 18B of an alternative embodiment of a proximal end of the electrosurgical tool cover of FIG. 12.

FIG. 18C is a side cross-sectional view taken along line 18B-18B of the electrosurgical tool cover of FIG. 12 illustrating the integrally connected tool tip cover portion and tool base cover portion, in which the end of the base cover portion is straight. While embodiments shown in FIGS. 6A and 18B show the tool cover having a tapered end at the base cover portion, it will be appreciated by one of ordinary skill in the art that the end of the base cover portion may be provided as a relatively straight, nontapered edge, as in FIG. 18C. The tapered end may allow the tool cover to be more easily removed from a cannula in which the tool cover and instrument has been placed. Alternately, a straight end may facilitate manufacturing the tool cover to accurate sizes, for example, by cutting the tool cover to the desired length.

Figure 19A:
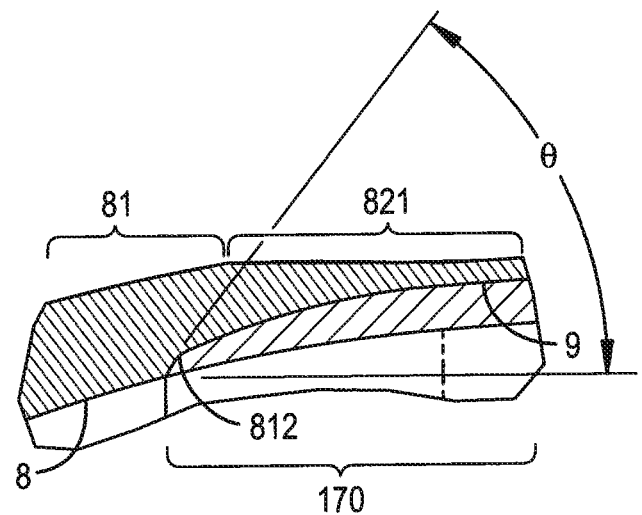
FIGS. 19A and 19B are partial cross-sectional views of the distal end portion of the overlap region of FIG. 18B and the proximal end portion of the overlap region of FIG. 18B, respectively.
Figure 19B:
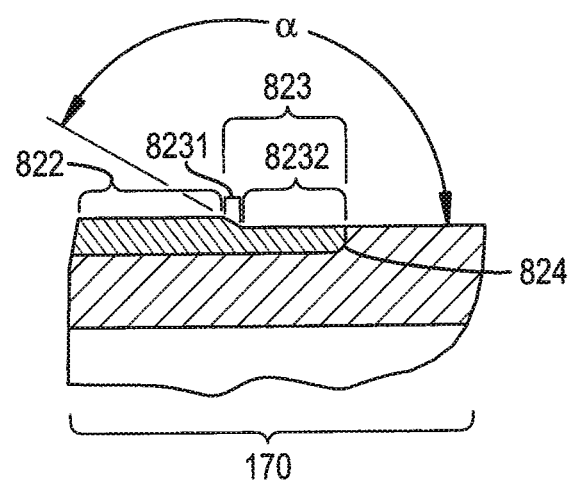

The connection or transition locations A, B between the tip cover portion 8 and the base cover portion 9 are disclosed in more detail with reference to FIG. 19A and FIG. 19B. The tip cover portion proximal part 82 surrounds the base cover portion distal part 91, as explained above for the electrosurgical tool cover 1.

Referring to FIG. 19A and FIG. 19B, the structure provides two transitional locations A, B where the structure changes from a multi-layer section to a single layer section. The first transitional location A is located at the recess 812, close to the tip cover portion proximal part 82. A detailed view of FIG. 19A illustrates the transition between the electrosurgical tip cover portion 8 and the base cover portion distal part 91. As shown in FIG. 19A, the thickness of the first material and the thickness of the second material vary along part of the length of the overlap region 170. The thickness of the first material decreases along at least part of the overlap region 170 in a direction away from the tip cover portion distal part 81. Further, the thickness of the second material increases along at least part of the overlap region 170 in a direction away from the tip cover portion distal part 81. The interface of the second material with the first material at a distal end of the overlap region 170, where the tip cover portion distal part 81 meets the tip end portion 910 of the base cover portion distal part 91, is disposed at a nonorthogonal angle with respect to a longitudinal axis of the structure of the tool cover 10. In an exemplary embodiment, the interface of the second material and the first material forms an angle θ ranging from about 20 degrees to about 75 degrees, for example, about 60 degrees with respect to the longitudinal axis of the hollow elongated structure of the tool cover 10. The interface of the second material with the first material at a distal end of the overlap region 17, shown in FIG. 8A, for example, may also be disposed at an nonorthogonal angle with respect to a longitudinal axis of the structure of the tool cover 1. For example, the interface may also form an angle θ ranging from about 20 degrees to about 75 degrees, as in the embodiment of FIG. 19A.

The tip end portion 910 of the base cover portion distal part 91 is shaped to have a smooth surface, such as a curved surface, instead of a sharp edged surface in order to avoid damages to the point of connection between parts. As discussed above, the curved surface reduces the possibility of disengagement or ruptures at the bonded area between the tip end portion 910 of the base cover portion 9 and the tip cover portion distal part 81 due to continuous motion or articulation of the electrosurgical instrument 5 by distributing stress over a larger area than, for example, a butt joint would. The larger area of overlap also increases the bond strength between the first and second materials. The base cover portion distal part 91, which forms part of the overlap region 170, has a tapered configuration along at least some of a length of the base cover portion distal part 91.

FIG. 19B is a detailed view of the second transitional location B, in which the overlap region 170 between the tip cover portion 8 and the base cover portion 9 ends and the structure transitions to only the second material of the base cover portion 9. In the embodiment, the tip cover portion proximal part 82 contacts the flange 9121 at the tip portion 921 of the base cover portion proximal part 92. At location B, the third section 823 is provided with a reduced outer diameter by providing a tapered section 8231 and a flat portion 8232 that define an angled step at the overlap region 170 proximate to the base cover portion proximal part 92. The tapered section 8231 extends from the second section 822 of the tip cover portion proximal part 82 to the flat portion 8232 of the third section 823. The tapered section 8231 can facilitate backing the electrosurgical instrument into a cannula during retraction of the electrosurgical instrument, for example, for removal from the patient or otherwise to adjust the positioning of the instrument. The tapered section 8231 may be tapered at an angle α, with respect to the top surface of the tool cover 10 along the flat portion 8232. In an exemplary embodiment, a can range from about 110-170 degrees, for example, a can be about 150 degrees. The flat portion 8232 of the third section 823 comprises a curved end 824 contacting the electrosurgical base cover portion 9 to avoid unwanted disengagement of the base cover portion 9 and the tip cover portion 8. By providing a curved surface at end 824, i.e., the location of the attachment between the tip cover portion 8 and the base cover portion 9, the length over which the materials are bonded together can provide a stronger bond than a direct, flat abutment of the materials against one another as would be provided by a butt joint, for example. While the end 824 is shown in FIG. 19B to be slightly angled, the curved surface at the end 824 may be angled at a greater degree, for example, at less than 90 degrees, as in FIG. 8C, to provide an increased bond strength by interlocking the two materials at the junction.

The electrosurgical tool cover 10 illustrated does not include protrusions or recesses on an inner wall thereof, however, those of ordinary skill in the art would appreciate that the same could be provided as described above with reference to the electrosurgical tool cover 1. In lieu of or in addition to providing protrusions or recesses for sealing, in order to provide retention and sealing for the electrosurgical cover 10, the cover relies on the inner diameter of the electrosurgical base cover portion 9 to fit against protrusions or ribs on the instrument 5 shaft. In particular, the hoop strength (i.e., the increased force of the tool cover in relation to the electrosurgical instrument as the inner diameter of the tool cover expands over ribs provided on the electrosurgical instrument) and the friction fit of the tool cover in relation to the electrosurgical instrument provides for tight retention between the tool cover and the electrosurgical instrument.

Figure 20A:
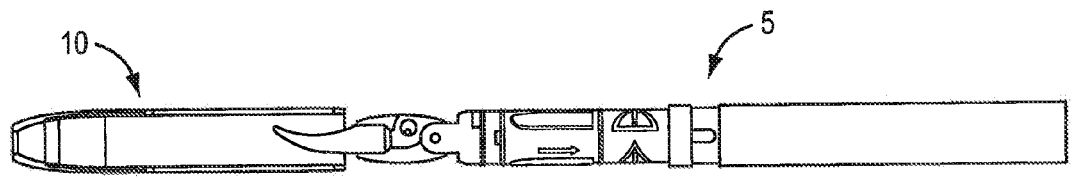
FIGS. 20A and 20B show cross-sectional side and perspective views of an electrosurgical tool cover during installation on an electrosurgical instrument in accordance with an exemplary embodiment of the present teachings.
Figure 20B:
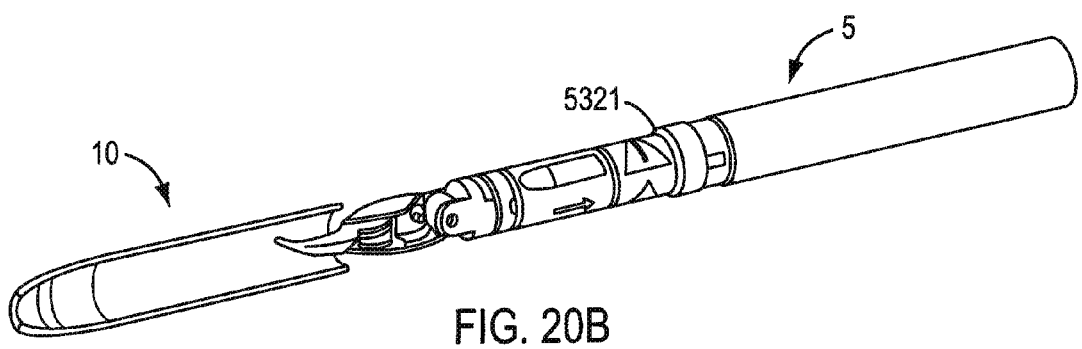
Figure 21A:
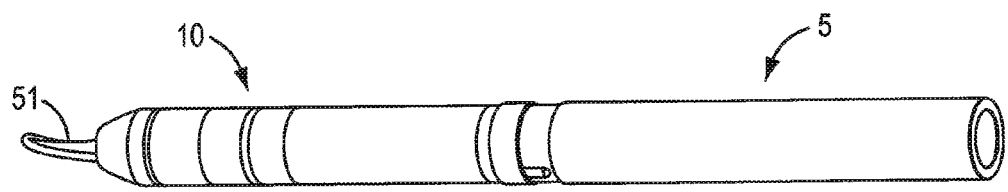
FIGS. 21A and 21B show perspective views of the electrosurgical tool cover of FIGS. 20A and 20B after installation on the electrosurgical instrument in accordance with an exemplary embodiment of the present teachings.
Figure 21B:
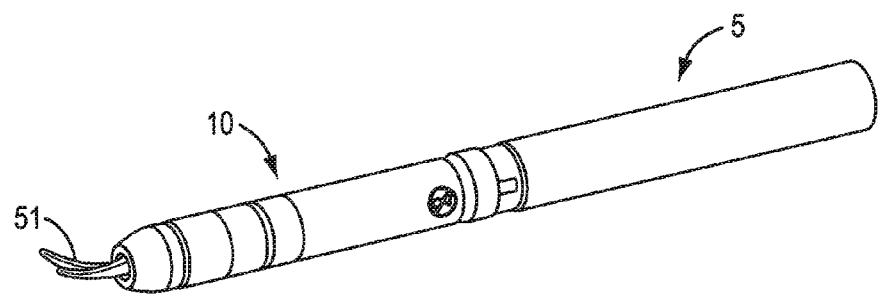

FIGS. 20A and 20B show cross-sectional views of the electrosurgical tool cover 10 being installed over the instrument end effector and wrist structure. FIGS. 21A through 21B are directed to perspective views of the electrosurgical tool cover 10 already installed. As mentioned, the tool cover 10 is intended to be in a tight connection, analogous to a sock fitting over an appendage, with the instrument 5 in order to avoid displacement of the cover during surgical procedures and to provide a seal between the tool cover and the instrument.

Figure 22:
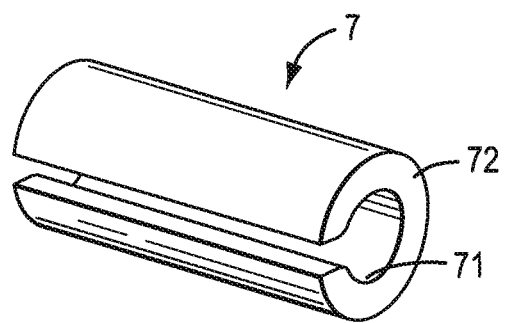
FIG. 22 is a perspective view of an exemplary embodiment of an installation tool for an electrosurgical tool cover in accordance with an exemplary embodiment of the present teachings.
Figure 23A:
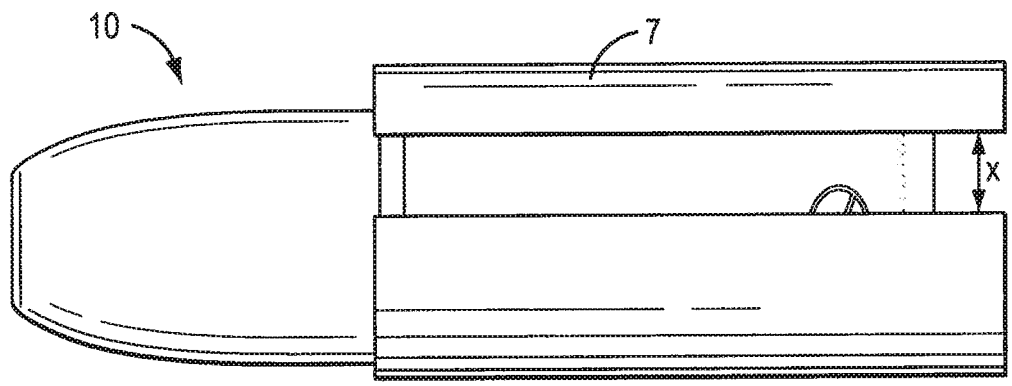
FIGS. 23A and 23B are side and cross-sectional views of an installation tool for the electrosurgical tool cover surrounding the electrosurgical tool cover and in use to install the electrosurgical tool cover on an electrosurgical instrument.
Figure 23B:
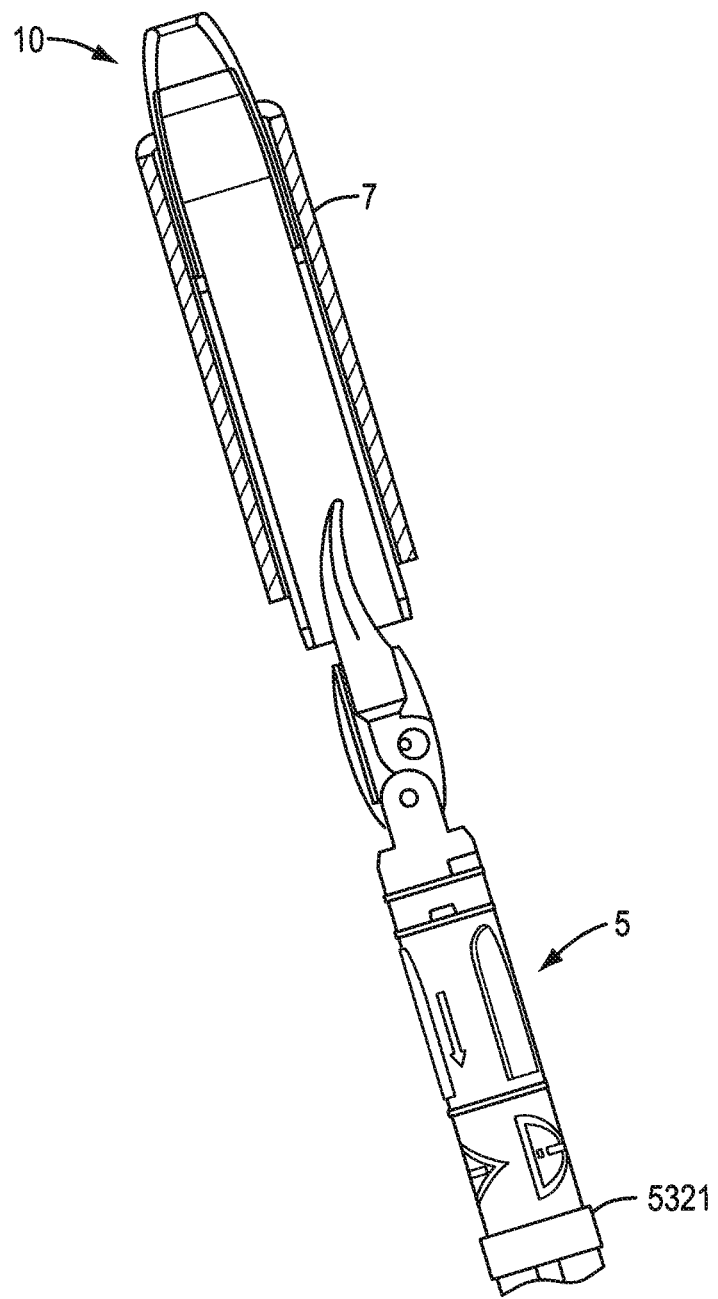

Referring now to FIGS. 22 through 23B, an exemplary embodiment of an installation tool 7 configured to assist with the installation of an electrosurgical tool cover, such as for example, tool covers 1 and 10, is illustrated. The installation tool 7 comprises a cylindrical hollow open ended body having a cutout section or slit X. The slit X provides an open space across the elongated installation tool body and avoids a continuous connection across the installation tool 7 cylindrical inner wall 71 and cylindrical outer wall 72. The slit X allows the expansion of the installation tool inner wall 71 diameter for an easy assembling of the installation tool 7 on the electrosurgical tool cover 1, 10 when positioning the electrosurgical tool cover 1, 10 inside the installation tool 7. The material for the installation tool 7 is selected from materials having flexibility and resilience properties, such as silicone, intended to cover and hold the electrosurgical tool cover 1, 10, while providing enough friction (e.g., grasping of the tool cover 1, 10) to assist with the sliding movement of the electrosurgical tool cover 1, 10 until the base cover portion 3, 9 of the tool cover 1, 10, more particularly the bottom end portion 323, 922 of the base cover portion proximal part 32, 92, which is rigid, stops with the shaft flange 5321 of the surgical instrument 5. The inner wall 71 diameter of the installation tool 7 is substantially similar to the outer wall diameter of the base cover portion 3, 9. FIG. 23B shows the installation process using the installation tool 7, wherein the installation tool 7 surrounds the electrosurgical tool cover 1, 10 during the process and is eventually removed from the electrosurgical tool cover 1, 10 outer surface, for example, after protrusions 4, 41, 42 engage on the respective radial recesses 411 or after the tool cover 1, 10 is otherwise properly seated relative to the electrosurgical instrument. The slit X facilitates the removal of the installation tool 7 from the electrosurgical tool cover 1, 10.

The composite structure including particularly the second material therefore provides for acceptable installation forces when the tool cover 1, 10 is installed on the instrument 5. For example, the second material may provide less sliding friction, as compared to the first material, to facilitate sliding the tool cover 1, 10 along and over the distal end of the electrosurgical instrument during installation. Further, the base cover portions 3, 9 of the tool covers 1, 10 may be configured to provide sufficient hoop strength when the tool cover 1, 10 is inserted over the electrosurgical instrument 5 to assist in providing a secure fit of the tool covers 1, 10 to the electrosurgical instrument shaft. Additionally, the materials forming the composite structure of the tool covers 1, 10 can exhibit sliding friction properties relative to the installation tool 7 that prevent or inhibit the installation tool 7 from sliding relative to the tool covers 1, 10 during the installation process.

In various exemplary embodiments, the second material from which the base cover portion of the tool covers 1, 10 is made may permit the tool covers to be manufactured with ink adhesion or laser etching to provide labeling thereon. In addition, in various exemplary embodiments, the second material is not translucent, in order to be able to be labeled so that a user is able to read the labeled material. Further, some electrosurgical instruments include a marking, such as, for example, a colored (e.g., orange or other color) marking, on the instrument that is covered by the tool cover 1, 10 during surgical use. Thus, as the second material is not translucent, the second material is able to effectively cover the instrument marking, which helps a user ensure proper placement of the tool cover over the electrosurgical instrument. Additionally, when the second material is not translucent, if tears or holes do develop, the tears or holes may be more visible to a user than if the material were translucent. In various exemplary embodiments, the tool cover may be made of a material that has a different color than the shaft of the electrosurgical instrument on which the tool cover is intended to be installed, which can help to distinguish and identify the tool cover as a removable (potentially disposable and/or reusable) component. By way of nonlimiting example only, the shaft of an electrosurgical instrument may be black and the tool cover may be gray.

Various exemplary embodiments of tool covers in accordance with the present teachings also may include outer surface portions that are configured to substantially reflect light emanating from proximal to the tool cover in a direction away from the base cover portion and toward the tip cover portion, in other words, in a direction toward the distal end of the tool cover and away from an operator at a proximal end of the electrosurgical instrument to which the cover is installed. In various exemplary embodiments, the outer surface portions of the tool covers can be highly polished to achieve reflection of light toward the distal end.

Also, in various exemplary embodiments, the materials from which the composite tool cover structures are made are sterilizable, biocompatible and capable of providing manufacturing of the tool covers at a reasonable cost.

Figure 24:
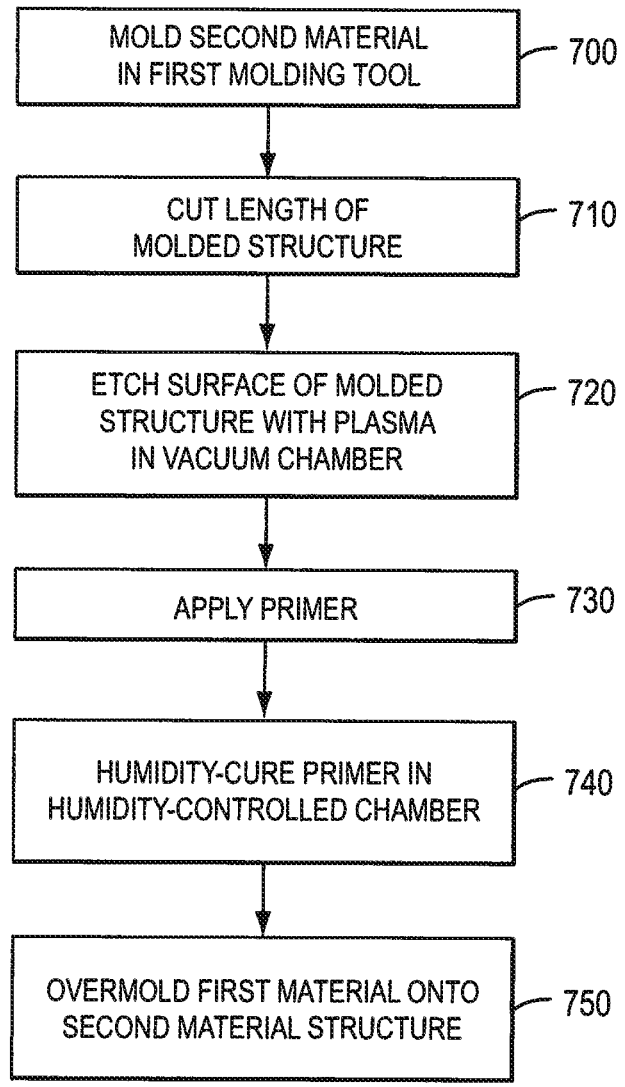
FIG. 24 is a flowchart illustrating a method of making the electrosurgical tool cover in accordance with at least one exemplary embodiment of the present teachings.

As mentioned above, in various exemplary embodiments, electrosurgical tool covers in accordance with the present teachings are made by overmolding the first and second materials (e.g., the tip cover portion and base cover portion) together. FIG. 24 is a flowchart illustrating an exemplary method of making a tool cover, such as, for example, the tool covers 1, 10. To join the first and second materials to one another (e.g., silicone and Pellethane®), in an exemplary embodiment, at step 700, a first molding tool, such as an injection molding tool, can be used to form a structure made from the second material (e.g., Pellethane®) which will form the base portion of the tool cover. When the first material is silicone, the first material may be, for example, Dow Silicone Q7-4780. When the second material is Pellethane®, the second material may be, for example, Lubrizol Pellethane 2363-90A. The formed structure made of the second material is thereafter cut to a desired length by, for example, a laser or other cutting device at step 710. The outer surface of the structure formed by the second material can then be etched with plasma in a vacuum chamber at step 720 to prevent migration of a later-applied primer.

The structure can then be removed from the vacuum chamber, and the structure formed of the second material is then primed at step 730. The primer can first be thinned with a solvent, such as Naphtha, then applied onto, for example, by spraying, the external surface of the structure formed at step 700 in a thin layer. The insert with the applied primer can then be humidity cured in a humidity-controlled chamber at step 740. In various exemplary embodiments, the primer can be cured for a time period ranging from about 1 hour to about 12 hours at a humidity ranging from about 30% to about 70%.

After the humidity curing process, the second material structure is removed from the humidity-controlled chamber and is inserted over a second molding tool, such as, for example, a pin or mandrel. Thereafter, at step 750, the first material, e.g., silicone, is overmolded onto the appropriate portion of the base portion structure held on the second molding tool support to create the integral, composite tool cover structure comprising the base cover portion and the tip cover portion.

Figure 25A:
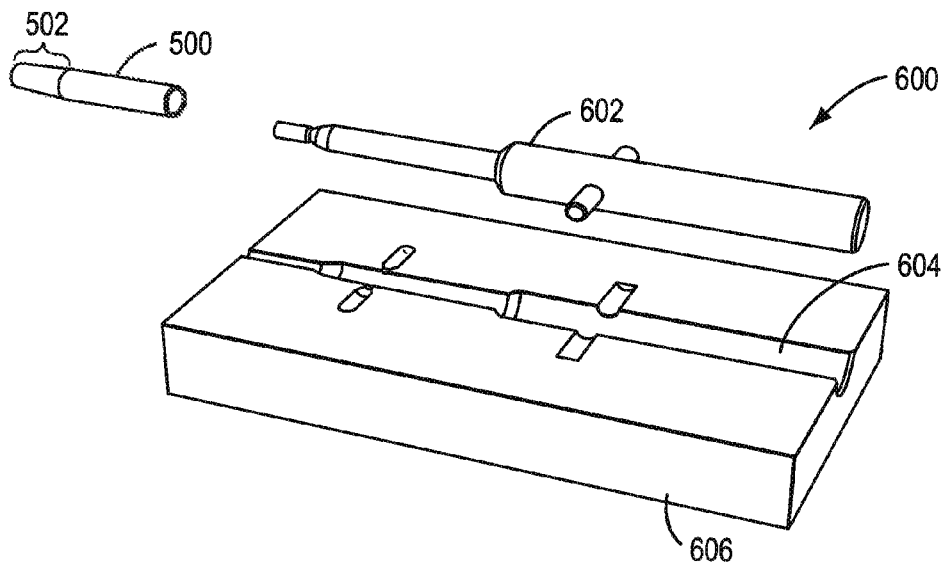
FIG. 25A is a perspective view of an overmold tool and a overmold tool component.
Figure 25B:
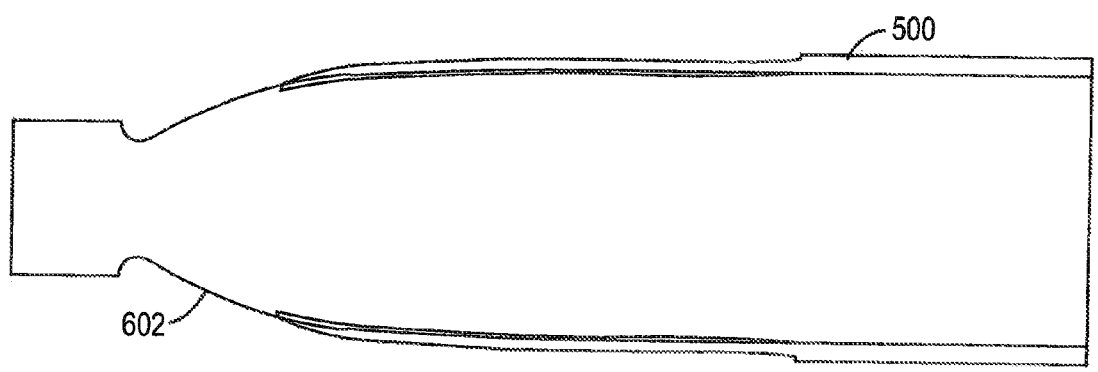
FIG. 25B is a side view of the overmold tool component, used in the method of making the electrosurgical tool cover in accordance with at least one exemplary embodiment of the present teachings.

With reference now to FIGS. 25A and 25B, an exemplary embodiment of a molding system 600 that can be used to perform step 750 of FIG. 24 is illustrated. The molding system 600 is a transfer molding system and includes a core pin 602 and a mold block 606. As described above with reference to FIG. 24, in an exemplary embodiment, the primed, humidity cured structure formed of the second material (labeled 500 in FIG. 25A) is inserted over the core pin 602. In various exemplary embodiments, as has been described herein with reference to the tool covers 1, 10, the second material structure 500 is sized smaller in the distal section 502 onto which the first material (e.g., silicone) is to be overmolded. To assist in preventing deformation during molding due to unintentional movement of the structure 500, it may be desirable to stretch the structure 500 on the core pin 602 to create a tight fit between the structure 500 and core pin 602, substantially as shown, for example, in FIG. 25B. The core pin 602 with the structure 500 thereon can be kept at or below room temperature, for example, at a temperature ranging from about 60 degrees Fahrenheit to about 90 degrees Fahrenheit.

The core pin 602 with the structure 500 fitted thereon is placed within an overmold tool cavity 604 defined within the mold block 606. Although not shown in the figures, a second mold block is placed over the core pin 602 placed within the cavity 604, as those ordinarily skilled in the art are familiar with. The mold block 606 may be heated to a temperature ranging from about 190 degrees Fahrenheit to about 235 degrees Fahrenheit in order to avoid melting the second material of the structure 500. Thereafter, the first material, e.g., silicone, is introduced into the cavities in the mold blocks and overmolded onto section 502 of the insert 500, as those ordinarily skilled in the art are familiar with when using transfer molding processes. The overmold blocks 606 are held together for a time period sufficient to cure the first material to the second material, for example, from about 3 minutes to about 6 minutes, thus creating the overall composite tool cover structure. The integral, composite tool cover structure is then removed from the molding system, including from the core pin 602.

While a plurality of ranges of specific properties have been described for various materials used in the composite structure, as discussed above, the recited ranges are of the materials in a pre-processed state, prior to processing the materials to make the composite tool cover structure.

Although various exemplary embodiments shown and described herein relate to surgical devices used for minimally invasive and/or robotically-controlled surgical procedures, those having ordinary skill in the art would understand that the structures and methods described may have a broad range of application to surgical devices, robotic and non-robotic, useful in a variety of applications. Those having ordinary skill in the art would understand how to modify the exemplary embodiments described herein to provide flexible, durable, electrically insulative structures useful for many types of surgical procedures, in particular for electrosurgical procedures.

Although certain exemplary embodiments and methods have been described in some detail, for clarity of understanding and by way of example, it will be apparent from the foregoing disclosure to those skilled in the art that variations, modifications, changes, and adaptations of such embodiments, structures, and methods may be made without departing from the scope of the present teachings and claims. For example, it will be appreciated that one of ordinary skill in the art will be able to employ a number of corresponding alternative and/or equivalent structural details, including dimensions, properties, and/or arrangements of parts Therefore, the above description should not be taken as limiting the scope of the invention, which is defined by the appended claims.

What is claimed is:

1. A cover for an electrosurgical instrument having a wrist structure and an end effector, the cover comprising:
  a hollow elongated structure comprising:
    a tip cover portion having a distal end with an opening therethrough sized to receive the end effector of the electrosurgical instrument, the tip cover portion being composed of a first electrically insulative material having a flexibility sufficient to allow the end effector to be manipulated while the end effector is received in the opening; and
    a base cover portion integrally connected to the tip cover portion, the base cover portion being composed of a second material having a higher tear strength than the first material,
    wherein the tip cover portion surrounds the base cover portion at an overlap region configured to receive the wrist structure of the electrosurgical instrument when the end effector is received in the opening.

2. The cover according to claim 1, wherein the second material has a higher tensile strength than the first material.

3. The cover according to claim 1, wherein the base cover portion has a first part surrounded by the tip cover portion to form the overlap region and a second part extending from the first part in a direction away from the tip cover portion.

4. The cover according to claim 3, wherein the tip cover portion does not surround the second part of the base cover portion.

5. The cover according to claim 3, wherein the second part of the base cover portion has a cylindrical configuration along a substantial length of the second part.

6. The cover according to claim 3, wherein the first part of the base cover portion is tapered along at least some of a length of the first part.

7. The cover according to claim 1, wherein a thickness of the first material and a thickness of the second material vary along at least part of a length of the overlap region.

8. The cover according to claim 7, wherein the thickness of the first material decreases along at least part of the overlap region in a direction away from the distal end of the tip cover portion.

9. The cover according to claim 7, wherein the thickness of the second material increases along at least part of the overlap region in a direction away from the distal end of the tip cover portion.

10. The cover according to claim 1, wherein an interface of the first material and the second material at a distal end portion of the overlap region is disposed at a nonorthogonal angle with respect to a longitudinal axis of the hollow elongated structure.

11. The cover according to claim 10, wherein the interface is disposed at an angle ranging from about 20 degrees to about 75 degrees with respect to the longitudinal axis of the hollow elongated structure.

12. The cover according to claim 3, wherein an outer surface of the hollow elongated structure defines an angled step at a location of the overlap region proximate the second part of the base cover portion.

13. The cover according to claim 1, wherein part of the tip cover portion including the distal end does not surround the base cover portion.

14. The cover according to claim 13, wherein the part of the tip cover portion that does not surround the base cover portion has a wall thickness that is larger than a wall thickness of the overlap region.

15. The cover according to claim 3, wherein a wall thickness of the overlap region is larger than a wall thickness of the second part of the base cover portion.

16. The cover according to claim 1, wherein the first material is silicone.

17. The cover according to claim 16, wherein the second material is a thermoplastic urethane.

18. The cover according to claim 1, wherein the second material is a polyurethane.

19. The cover according to claim 18, wherein the second material is a thermoplastic urethane.

20. The cover according to claim 1, wherein the second material is opaque.

21. The cover according to claim 1, wherein the first material is overmolded with the second material in the overlap region.

22. The cover according to claim 21, wherein the first material is silicone and the second material is a thermoplastic urethane.

23. The cover according to claim 1, wherein the base cover portion includes at least one protrusion extending inwardly from an inner wall of the base cover portion.

24. The cover according to claim 23, wherein the at least one protrusion is configured to engage with the electrosurgical instrument to retain the cover on the electrosurgical instrument.

25. The cover according to claim 1, wherein the hollow elongated structure has an outer surface that reflects light emanating from proximal to the cover in a direction away from the base cover portion and toward the tip cover portion.

26. The cover according to claim 1, wherein the hollow elongated structure has a polished outer surface.

27. A cover for an electrosurgical instrument having a wrist structure and an end effector, the cover comprising:
    a hollow elongated composite material structure having an end with an opening therethrough sized to receive the end effector of the electrosurgical instrument, the hollow structure comprising:
        a first distal region comprising the end with the opening, the first distal region being composed of a first electrically insulative material having a flexibility sufficient to allow the end effector of the electrosurgical instrument to be manipulated while the end effector is received in the opening,
        a second proximal region composed of a second material having a higher tear strength than the first material, and
        a transition region in which the first material surrounds the second material, the transition region being disposed between the first distal region and the second proximal region.

28. The cover according to claim 27, wherein the second material has a higher tensile strength than the first material.

29. A cover for an electrosurgical instrument having a wrist structure and an end effector, the cover comprising:
    a hollow elongated structure comprising:
        a tip cover portion having a distal end with an opening therethrough sized to receive the end effector of the electrosurgical instrument, the tip cover portion being composed of a first, electrically insulative material having a flexibility sufficient to allow the end effector to be manipulated while the end effector is received in the opening; and
        a base cover portion integrally connected to the tip cover portion, the base cover portion being composed of a second material having a higher tensile strength than the first material,
    wherein the tip cover portion surrounds the base cover portion at an overlap region configured to receive the wrist structure of the electrosurgical instrument when the end effector is received in the opening.

30. The cover according to claim 29, wherein a ratio of the tensile strength of the second material to the tensile strength of the first material is at least 2:1.

* * * * *